(12) United States Patent
An et al.

(10) Patent No.: US 11,883,433 B1
(45) Date of Patent: Jan. 30, 2024

(54) CHIMERIC ANTIGEN RECEPTOR COMPRISING ANTI-MESOTHELIN SCFV, AND USE THEREOF

(71) Applicant: CELLENGENE INC., Seongnam-si (KR)

(72) Inventors: Jae Hyung An, Seongnam-si (KR); Na Kyung Han, Seoul (KR)

(73) Assignee: CELLENGENE INC., Seongnam-si (KR)

( * ) Notice: Subject to any disclaimer, the term of this patent is extended or adjusted under 35 U.S.C. 154(b) by 0 days.

(21) Appl. No.: 18/255,814

(22) PCT Filed: May 25, 2022

(86) PCT No.: PCT/KR2022/007425
§ 371 (c)(1),
(2) Date: Jun. 2, 2023

(87) PCT Pub. No.: WO2022/250450
PCT Pub. Date: Dec. 1, 2022

(30) Foreign Application Priority Data

May 26, 2021 (KR) .................. 10-2021-0067904

(51) Int. Cl.
| | |
|---|---|
| *C07K 16/30* | (2006.01) |
| *A61K 39/395* | (2006.01) |
| *A61K 35/17* | (2015.01) |
| *C07K 16/18* | (2006.01) |
| *A61P 35/00* | (2006.01) |
| *C12N 5/0783* | (2010.01) |
| *C12N 15/86* | (2006.01) |
| *C12N 15/13* | (2006.01) |
| *C12N 15/62* | (2006.01) |
| *C07K 14/47* | (2006.01) |
| *A61K 39/00* | (2006.01) |

(52) U.S. Cl.
CPC .......... *A61K 35/17* (2013.01); *A61K 39/4631* (2023.05); *A61P 35/00* (2018.01); *C07K 14/47* (2013.01); *C07K 16/30* (2013.01); *A61K 2039/505* (2013.01); *A61K 2239/21* (2023.05); *C12N 5/0638* (2013.01); *C12N 15/62* (2013.01); *C12N 15/86* (2013.01)

(58) Field of Classification Search
CPC .. A61K 35/17; A61K 39/4631; A61K 39/395; A61K 2039/505; A61K 2239/21; A61P 35/00; C07K 14/47; C07K 16/30
See application file for complete search history.

(56) References Cited

U.S. PATENT DOCUMENTS

| | | | |
|---|---|---|---|
| 11,795,215 B2 * | 10/2023 | An ............... | A61K 39/4611 |
| 2016/0311917 A1 | 10/2016 | Beatty et al. | |
| 2018/0244796 A1 | 8/2018 | Wang et al. | |
| 2019/0000944 A1 | 1/2019 | Brogdon et al. | |
| 2020/0289646 A1 | 9/2020 | Wesche et al. | |
| 2020/0407460 A1 | 12/2020 | Beatty et al. | |
| 2021/0347870 A1 | 11/2021 | Ahn et al. | |
| 2023/0151082 A1* | 5/2023 | An ............... | C12N 5/0636 424/93.21 |

FOREIGN PATENT DOCUMENTS

| | | | | |
|---|---|---|---|---|
| AU | 2021245153 A1 * | 2/2022 | ............ | A61K 35/17 |
| CA | 3133678 A1 * | 1/2022 | ............ | A61K 35/17 |
| CN | 106467573 A | 3/2017 | | |
| CN | 114364702 A * | 4/2022 | ............ | A61K 35/17 |
| JP | 2020519295 A | 7/2020 | | |
| JP | 2021035948 A | 3/2021 | | |
| KR | 1020160098259 A | 8/2016 | | |
| KR | 1020200090598 A | 7/2020 | | |
| KR | 102309543 B1 | 10/2021 | | |
| WO | 2017052241 A1 | 3/2017 | | |
| WO | 2020043152 A1 | 3/2020 | | |
| WO | WO-2022030730 A1 * | 2/2022 | ............ | A61K 35/17 |

OTHER PUBLICATIONS

Korean Notice of Allowance in KR 10-2022-0064250 and dated Feb. 8, 2023.
Dainty et al., "Overexpression of folate binding protein and mesothelin are associated with uterine serous carcinoma", Gynecologic Oncology, 105, 2007, 563-570.
He et al., "Killing cervical cancer cells by specific chimeric antigen receptor-modified T cells", Journal of Reproductive Immunology, 139, 2020, 103115.
Kiesgen et al., "Chimeric Antigen Receptor (CAR) T-Cell Therapy for Thoracic Malignancies", Journal of Thoracic Oncology, vol. 13, No. 1, 2017, 16-26.
Morello et al,. "Mesothelin-Targeted CARs: Driving T Cells to Solid Tumors", Cancer Discovery, Feb. 2016, 0F1-0F15.
O'Hara et al., "Meshothelin as a target for chimeric antigen receptor-modified T cells as anticancer therapy", Immunotherapy, 2016, 8(4), 449-460.
Steinbach et al., "Mesothelin, a possible target for immunotherapy, is expressed in primary AML cells", European Journal of Haematology, Jul. 2, 2007, 281-286.
Written Decision on Registration in KR 10-2022-0064250 and dated Feb. 8, 2023.

* cited by examiner

*Primary Examiner* — Hong Sang
(74) *Attorney, Agent, or Firm* — CANTOR COLBURN LLP

(57) ABSTRACT

Provided is an anti-mesothelin chimeric antigen receptor that specifically binds to mesothelin. The anti-mesothelin chimeric antigen receptor according to an aspect exhibits a specific binding ability for mesothelin, and thus, may be useful for preventing or treating cancer in which mesothelin is overexpressed.

16 Claims, 17 Drawing Sheets

Specification includes a Sequence Listing.

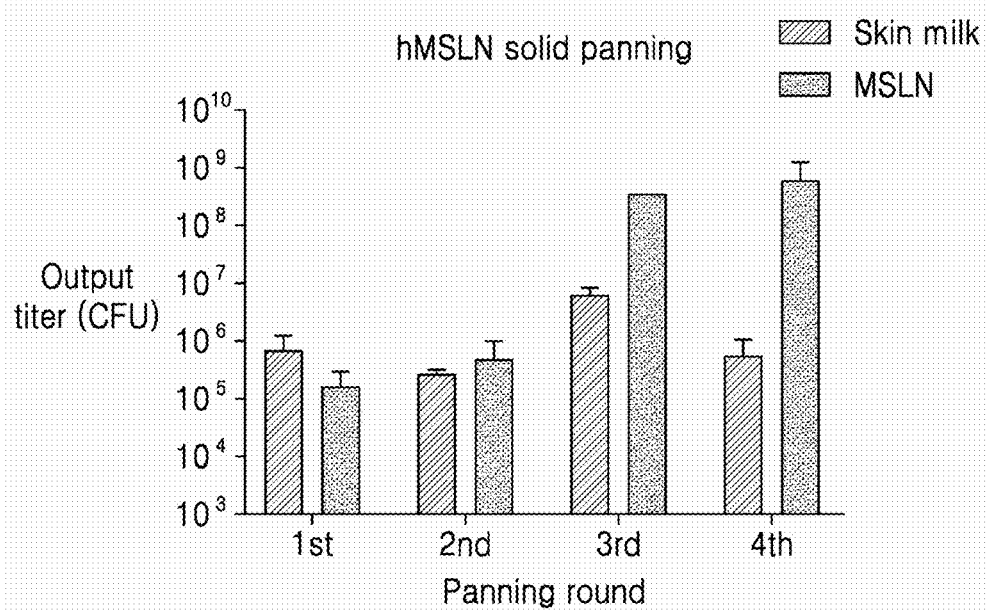

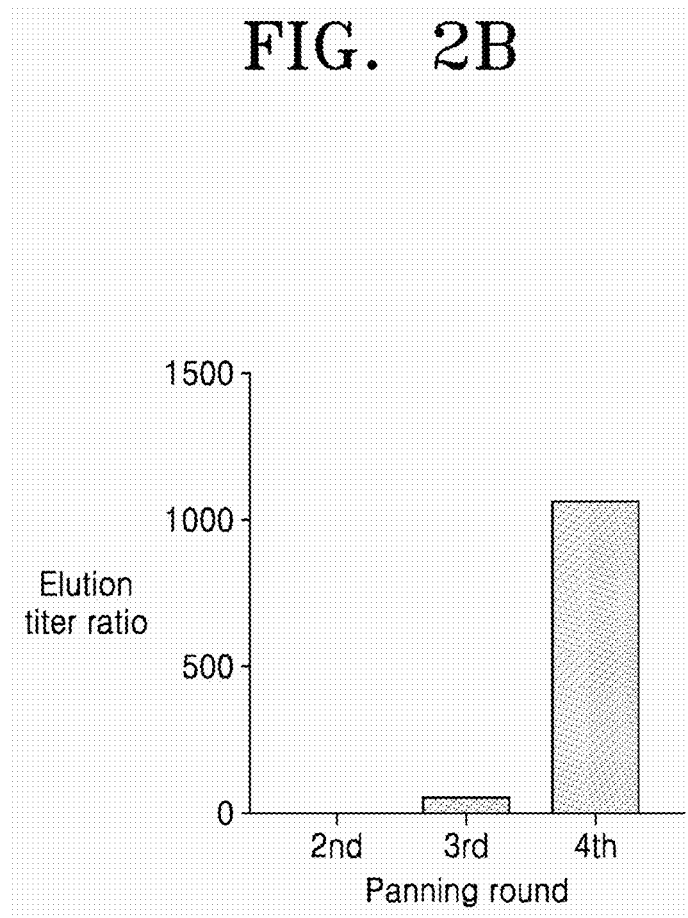

SEQUENCE LISTING

<160> NUMBER OF SEQ ID NOS: 15

<210> SEQ ID NO 1
<211> LENGTH: 5
<212> TYPE: PRT
<213> ORGANISM: Artificial
<220> FEATURE:
<223> OTHER INFORMATION: HCDR1 of MSLN3

<400> SEQUENCE: 1

Asp Tyr Ala Met Ser
1               5

<210> SEQ ID NO 2
<211> LENGTH: 17
<212> TYPE: PRT
<213> ORGANISM: Artificial
<220> FEATURE:
<223> OTHER INFORMATION: HCDR2 of MSLN3

<400> SEQUENCE: 2

Ala Ile Ser Ser Ser Gly Gly Thr Thr Tyr Tyr Ala Asp Ser Val Lys
1               5                   10                  15

Gly

<210> SEQ ID NO 3
<211> LENGTH: 12
<212> TYPE: PRT
<213> ORGANISM: Artificial
<220> FEATURE:
<223> OTHER INFORMATION: HCDR3 of MSLN3

<400> SEQUENCE: 3

Glu Glu Glu Gly Glu Trp Arg Glu Tyr Phe Asp Val
1               5                   10

<210> SEQ ID NO 4
<211> LENGTH: 11
<212> TYPE: PRT

```
<213> ORGANISM: Artificial
<220> FEATURE:
<223> OTHER INFORMATION: LCDR1 of MSLN3

<400> SEQUENCE: 4

Arg Ala Ser Gln Ser Ile Ser Ser Tyr Leu Asn
1               5                   10

<210> SEQ ID NO 5
<211> LENGTH: 7
<212> TYPE: PRT
<213> ORGANISM: Artificial
<220> FEATURE:
<223> OTHER INFORMATION: LCDR2 of MSLN3

<400> SEQUENCE: 5

Ala Thr Ser Thr Leu Gln Ser
1               5

<210> SEQ ID NO 6
<211> LENGTH: 9
<212> TYPE: PRT
<213> ORGANISM: Artificial
<220> FEATURE:
<223> OTHER INFORMATION: LCDR3 of MSLN3

<400> SEQUENCE: 6

Gln Gln Ser Tyr Thr Phe Pro Tyr Thr
1               5

<210> SEQ ID NO 7
<211> LENGTH: 121
<212> TYPE: PRT
<213> ORGANISM: Artificial
<220> FEATURE:
<223> OTHER INFORMATION: VH of MSLN3

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Glu Gly Glu Trp Arg Glu Tyr Phe Asp Val Trp Gly
            100                 105                 110

Gln Gly Thr Leu Val Thr Val Ser Ser
        115                 120

<210> SEQ ID NO 8
<211> LENGTH: 107
<212> TYPE: PRT
<213> ORGANISM: Artificial
<220> FEATURE:
<223> OTHER INFORMATION: VL of MSLN3

<400> SEQUENCE: 8
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
                35                  40                  45

Tyr Ala Thr Ser Thr Leu Gln Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Phe Pro Tyr
                85                  90                  95

Thr Phe Gly Gln Gly Thr Lys Val Glu Ile Lys
                100                 105
```

<210> SEQ ID NO 9
<211> LENGTH: 630
<212> TYPE: PRT
<213> ORGANISM: Artificial
<220> FEATURE:
<223> OTHER INFORMATION: mesothelin

<400> SEQUENCE: 9

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
                35                  40                  45

Asp Gly Val Leu Ala Asn Pro Pro Asn Ile Ser Ser Leu Ser Pro Arg
50                      55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
                100                 105                 110

Glu Asp Leu Asp Ala Leu Pro Leu Asp Leu Leu Leu Phe Leu Asn Pro
            115                 120                 125

Asp Ala Phe Ser Gly Pro Gln Ala Cys Thr Arg Phe Phe Ser Arg Ile
130                     135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
                180                 185                 190

Pro Gly Arg Phe Val Ala Glu Ser Ala Glu Val Leu Leu Pro Arg Leu
            195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255
```

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
            275                 280                 285

Leu Arg Pro Arg Phe Arg Arg Glu Val Glu Lys Thr Ala Cys Pro Ser
        290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
610                 615                 620

Leu Ala Ser Thr Leu Ala
625                 630

<210> SEQ ID NO 10
<211> LENGTH: 63
<212> TYPE: DNA
<213> ORGANISM: Artificial
<220> FEATURE:
<223> OTHER INFORMATION: CD8 sequence

<400> SEQUENCE: 10

```
atggccttac cagtgaccgc cttgctcctg ccgctggcct tgctgctcca cgccgccagg    60
ccg                                                                  63
```

<210> SEQ ID NO 11
<211> LENGTH: 738
<212> TYPE: DNA
<213> ORGANISM: Artificial
<220> FEATURE:
<223> OTHER INFORMATION: MSLN3 scFv sequence

<400> SEQUENCE: 11

```
gaagtacagt tggtcgaaag tggcggtggc ctcgtgcaac cgggtggttc actgcgtctg    60
agctgcgccg cctcgggttt tactttctct gattatgcaa tgtcttgggt tcgtcaggcg   120
ccgggcaagg gtctcgaatg ggtttcagca atctcttctt ctggtggtac tacttactat   180
gccgattcag tgaagggtcg ctttaccatt tcccgtgaca actctaagaa tactctgtat   240
ctgcagatga actcgctgcg tgccgaagac acggccgtct attattgcgc caagaagaa    300 gaaggtgaat ggcgtgaata cttcgatgtt tggggtcagg gcactttagt gaccgtctca   360
tcgggtggag gcggttcagg cggaggtgga tccggcggtg gcggatcgga cattcaaatg   420
acgcagagtc cctcctcact gagtgctagc gtgggcgatc gtgtgacaat acttgtcgc   480 gctagccagt ctatctcttc ttacctgaac tggtatcagc agaaaccggg caaggcgcca   540
aaattgctga tttacgcaac ttccactctg cagtctggtg taccgtcccg tttctctggc   600
agcggttctg gtacggattt taccctgacc atctcaagcc tccagcctga agattttgcc   660
acctattatt gtcagcaatc ttacactttt ccgtacacgt tcgggcaggg aactaaagtg   720
gaaattaaag ccagcacc                                                 738
```

<210> SEQ ID NO 12
<211> LENGTH: 135
<212> TYPE: DNA
<213> ORGANISM: Artificial
<220> FEATURE:
<223> OTHER INFORMATION: CD8 hinge sequence

<400> SEQUENCE: 12

```
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135
```

<210> SEQ ID NO 13
<211> LENGTH: 72
<212> TYPE: DNA
<213> ORGANISM: Artificial
<220> FEATURE:
<223> OTHER INFORMATION: CD8 TM sequence

<400> SEQUENCE: 13

```
atctacatct gggcgccctt ggccgggact tgtgggtgtcc ttctcctgtc actggttatc    60 acccttact gc                                                         72
```

<210> SEQ ID NO 14
<211> LENGTH: 126
<212> TYPE: DNA
<213> ORGANISM: Artificial
<220> FEATURE:

```
<223> OTHER INFORMATION: 4-1BB sequence

<400> SEQUENCE: 14
aaacggggca gaaagaaact cctgtatata ttcaaacaac catttatgag accagtacaa        60
actactcaag aggaagatgg ctgtagctgc cgatttccag aagaagaaga aggaggatgt       120
gaactg                                                                 126

<210> SEQ ID NO 15
<211> LENGTH: 337
<212> TYPE: DNA
<213> ORGANISM: Artificial
<220> FEATURE:
<223> OTHER INFORMATION: CD3z sequence

<400> SEQUENCE: 15
agagtgaagt tcagcaggag cgcagacgcc cccgcgtaca cagcagggcc agaaccagct        60
ctataacgag ctcaatctag gacgaagaga ggagtacgat gttttggaca agagacgtgg       120
ccgggaccct gagatggggg gaaagccgag aaggaagaac cctcaggaag gcctgtacaa       180
tgaactgcag aaagataaga tggcggaggc ctacagtgag attgggatga aaggcgagcg       240
ccggaggggc aaggggcacg atggcctttta ccagggtctc agtacagcca ccaaggacac       300
ctacgacgcc cttcacatgc aggccctgcc ccctcgc                                337
```

CHIMERIC ANTIGEN RECEPTOR COMPRISING ANTI-MESOTHELIN SCFV, AND USE THEREOF

CROSS-REFERENCE TO RELATED APPLICATIONS

The present application is a U.S. national phase application of International Application No. PCT/KR2022/007425 filed on May 25, 2022, which claims priority to/from and the benefit of Korean Application No. 10-2021-0067904 filed on May 26, 2021, each of which is incorporated herein by reference in its entirety for all purposes.

SEQUENCE LISTING

The present application contains a Sequence Listing which has been submitted electronically in ASCII format and is hereby incorporated by reference in its entirety. Said ASCII copy, created on Jun. 1, 2023, is named "96N1661.TXT" and is 11,965 bytes in size.

TECHNICAL FIELD

The disclosure relates to an anti-mesothelin chimeric antigen receptor that specifically binds to mesothelin, and use thereof.

BACKGROUND ART

Recently, immuno-anticancer agents such as immune checkpoint inhibitors and a CAR-T cell therapeutic agent have demonstrated their effectiveness in various cancers, but it has been reported that solid cancers do not respond significantly to these new types of immuno-anticancer agents. This is presumed to be because the fibrous tissue surrounding the tumor interferes with the immunotherapeutic response and makes drug delivery difficult. Therefore, as a specific and more effective CAR-T cancer treatment method, there is an emerging need for research on how to develop an antibody that targets a protein specifically over-expressed on the surface of solid cancer cells as a cancer antigen, and to effectively treat solid cancer by using the antibody.

On the other hand, mesothelin is a glycoprotein anchored to a surface of a cell by a glycosylphosphatidylinositol (GPI) domain, and is normally expressed at a low level restrictedly in the mesothelium surrounding the cavities and internal organs in the human body, but is known to be abundantly expressed in cancers such as pancreatic cancer, mesothelioma, ovarian cancer, non-small cell lung cancer, etc.

DISCLOSURE

Technical Problem

An aspect is to provide an anti-mesothelin antibody, or an antigen-binding fragment thereof.

Another aspect is to provide isolated nucleic acid encoding the anti-mesothelin antibody or the antigen-binding fragment thereof.

Still another aspect is to provide a vector including the isolated nucleic acid.

Still another aspect is to provide an isolated host cell transformed by the vector.

Still another aspect is to provide a method of preparing anti-mesothelin antibodies, including expressing the antibody by culturing the isolated host cell Still another aspect is to provide a chimeric antigen receptor including an antigen-binding domain, a hinge domain, a transmembrane domain, and an intracellular signaling domain.

Still another aspect is to provide a polynucleotide encoding the chimeric antigen receptor.

Still another aspect is to provide a vector including the polynucleotide.

Still another aspect is to provide an isolated cell transformed by the vector.

Still another aspect is to provide a pharmaceutical composition including the isolated cells; medical use of the cells; and a method of preventing or treating cancer, including administering the cells in a therapeutically effective amount to a subject.

Other objects and advantages of the present application will become more apparent from the following detailed description in conjunction with the appended claims and the drawings. Since the content not described in this specification may be sufficiently recognized and inferred by those skilled in the related art or a similar art thereto, the description thereof will be omitted.

Technical Solution

Each description and embodiment disclosed in the present application may also be applied to other descriptions and embodiments. That is, all combinations of various elements disclosed in the application fall within the scope of the application. In addition, it should not be construed that the scope of the present application is limited by the detailed description described below.

An aspect provides an anti-mesothelin antibody, or an antigen-binding fragment thereof.

The "mesothelin (MSLN)" is a cell surface glycoprotein (NCBI Gene ID: 10232) with a total amino acid length of 630 aa, and is selectively expressed in some cells, particularly certain tumor cells, and the amino acid sequence of the mesothelin protein is shown below:

(SEQ ID NO: 9)
MALPTARPLLGSCGTPALGSLLFLLFSLGWVQPSRTLAGETGQEAAPLDG

NVLAPPNISSLSPRQLLGFPCAEVSGLSTERVRELAVALAQKNVKLSTEQ

LRCLAHRLSEPPEDLDALPLDLLLFLNPDAFSGPQACTRFFSRITKANVD

LLPRGAPERQRLLPAALACWGVRGSLLSEADVRALGGLACDLPGRFVAES

AEVLLPRLVSCPGPLDQDQQEAARAALQGGGPPYGPPSTWSVSTMDALRG

LLPVLGQPIIRSIPQGIVAAWRQRSSRDPSWRQPERTILRPRFRREVEKT

ACPSGKKAREIDESLIFYKKWELEACVDAALLATQMDRVNAIPFTYEQLD

VLKHKLDELYPQGYPESVIQHLGYLFLKMSPEDIRKWNVTSLETLKALLE

VNKGHEMSPQAPRRPLPQVATLIDRFVKGRGQLDKDTLDTLTAFYPGYLC

SLSPEELSSVPPSSIWAVRPQDLDTCDPRQLDVLYPKARLAFQNMNGSEY

FVKIQSFLGGAPTEDLKALSQQNVSMDLATFMKLRTDAVLPLTVAEVQKL

LGPHVEGLKAEERHRPVRDWILRQRQDDLDTLGLGLQGGIPNGYLVLDLS

MQEALSGTPCLLGPGPVLTVLALLLASTLA

Mesothelin shows low expression in normal mesothelial cells, but is highly expressed in solid cancer (solid tumor), and has been confirmed to be overexpressed in esophageal cancer, breast cancer, triple-negative breast cancer (TNBC), gastric cancer, cholangiocarcinoma, pancreatic cancer, colon cancer, lung cancer, thymic carcinoma, mesothelioma, ovarian cancer, endometrial cancer, cervical cancer, uterin serous carcinoma (USC), and acute myeloid leukemia (AML), etc. (Cancer Discov. 2016 February; 6(2):133-46.; J Reprod Immunol. 2020; 139:103115.; Gynecol Oncol. 2007; 105 (3):563-570.; Eur J Haematol. 2007; 79(4):281-286).

In an embodiment, MSLN3 was discovered as an antibody that specifically binds to a target antigen, mesothelin, through phage display antibody library panning.

The term "antibody", used herein, is a generic term for proteins involved in in vivo immunity by selectively acting on antigens, and the types are not particularly limited. A heavy chain and a light chain of the antibody have an antigen-binding site that recognizes an epitope including a variable region, and antigen specificity appears according to a change in the sequence of the variable region. The variable region of the antigen-binding site is divided into a framework region (FR) with low variability and a complementarity determining region (CDR) with high variability, and both the heavy chain and the light chain have three CDR sites divided into CDR1, 2, and 3, and four FR sites. The CDRs of each chain are typically named CDR1, CDR2, and CDR3 sequentially starting from the N-terminus, and are identified by the chain in which a particular CDR is located.

The term, "complementarity determining region", used herein, refers to a site that confers binding specificity with an antigen among variable regions of an antibody.

The term "epitope", used herein, refers to a specific three-dimensional molecular structure within an antigen molecule to which an antibody may specifically bind.

The antibody includes all of monoclonal antibodies, multispecific antibodies, human antibodies, humanized antibodies, and chimeric antibodies (for example, humanized murine antibodies). In addition, the antibody may include diabodies, triabodies, and tetrabodies.

In the present specification, an antibody includes an "antigen-binding fragment" or an "antibody fragment" of an antibody having antigen-binding ability. The antigen-binding fragment may be an antibody fragment including at least one complementarity determining region, for example, one selected from the group consisting of scFv, (scFv)2, scFv-Fc, Fab, Fab', and F(ab')2. Among antibody fragments, Fab has a structure having variable regions of the light chain and the heavy chain, a constant region of the light chain, and a first constant region (CH1) of the heavy chain, and has one antigen-binding site. Fab' differs from Fab in that Fab' has a hinge region including one or more cysteine residues at the C-terminus of the CH1 domain of the heavy chain. An F(ab')2 antibody is produced when a cysteine residue in the hinge region of Fab' forms a disulfide bond. Fv is the smallest antibody fragment having only a heavy chain variable region and a light chain variable region. In a two-chain Fv, a heavy chain variable region and a light chain variable region are connected by a non-covalent bond. In a single-chain Fv (scFv), a variable region of the heavy chain and a variable region of the light chain may be covalently linked by a peptide linker, or may be directly linked at the C-terminus, and thus, a single-chain Fv may form a dimer-like structure, like a two-chain Fv.

An anti-mesothelin antibody according to an aspect or an antigen-binding fragment thereof may include: a heavy chain CDR1 including an amino acid sequence consisting of SEQ ID NO: 1; a heavy chain CDR2 including an amino acid sequence consisting of SEQ ID NO: 2; a heavy chain CDR3 including an amino acid sequence consisting of SEQ ID NO: 3; a light chain CDR1 including an amino acid sequence consisting of SEQ ID NO: 4; a light chain CDR2 including an amino acid sequence consisting of SEQ ID NO: 5; and a light chain CDR3 including an amino acid sequence consisting of SEQ ID NO: 6.

The anti-mesothelin antibody or the antigen-binding fragment thereof may include a heavy chain variable region including a sequence having sequence homology with the amino acid sequence consisting of SEQ ID NO: 7 of 80% or more, preferably sequence homology of 90% or more, preferably sequence homology of 95% or more, or more preferably sequence homology of 100%.

The anti-mesothelin antibody or the antigen-binding fragment thereof may include a light chain variable region including a sequence having sequence homology with the amino acid sequence consisting of SEQ ID NO: 8 of 80% or more, preferably sequence homology of 90% or more, preferably sequence homology of 95% or more, or more preferably sequence homology of 100%.

The anti-mesothelin antibody or the antigen-binding fragment thereof may include a heavy chain variable region including an amino acid sequence consisting of SEQ ID NO: 7, or a light chain variable region including an amino acid sequence consisting of SEQ ID NO: 8.

In an embodiment, the anti-mesothelin antibody or the antigen-binding fragment thereof may be an anti-mesothelin antibody scFv (anti-MSLN3 scFv) including a heavy chain variable region including an amino acid sequence consisting of SEQ ID NO: 7, or a light chain variable region including an amino acid sequence consisting of SEQ ID NO: 8.

The antibody according to an aspect, or the antigen-binding fragment thereof may include a sequence of the anti-mesothelin antibody described herein, which specifically binds to mesothelin, as well as biological equivalents thereof, within a range that the antibody or the antigen-binding fragment thereof may specifically recognize mesothelin. For example, additional changes may be made to the amino acid sequence of the antibody to further improve its binding affinity, and/or other biological properties.

For example, the amino acid sequence of the antibody may be substituted through conservative substitution. The term "conservative substitution", used herein, refers to a modification of a polypeptide the modification including substituting one or more amino acids with amino acids having similar biochemical properties that do not result in a loss of a biological or biochemical function of the polypeptide. A "conservative amino acid substitution" is a substitution in which an amino acid residue is replaced with an amino acid residue having a similar side chain. Groups of amino acid residues with similar side chains have been defined in the art. These groups include: amino acids with basic side chains (for example, lysine, arginine, and histidine); amino acids with acidic side chains (for example, aspartic acid, and glutamic acid), amino acids with uncharged polar side chains (for example, glycine, asparagine, glutamine, serine, threonine, tyrosine, and cysteine), amino acids with non-polar side chains (for example, alanine, valine, leucine, isoleucine, proline, phenylalanine, methionine, and tryptophan); amino acids with beta-branched side chains (for example, threonine, valine, and isoleucine), and amino acids with aromatic side chains (for example, tyrosine, phenylalanine, tryptophan, and histidine). It may be expected that the antibody according to an aspect may still retain its original activity even though some amino acid sequences of the antibody are substituted through conservative amino acid substitutions.

In consideration of variation having the above-described biologically equivalent activity, the antibody of an aspect or a nucleic acid molecule encoding the same are interpreted to include sequences showing substantial identity with the sequence described with sequence numbers. The substantial identity refers to that a sequence shows homology of at least 61%, more preferably homology of at least 70%, even more preferably homology of at least 80%, even more preferably homology of at least 90%, even more preferably homology of at least 95%, and the most preferably homology of at least 98%, when the above sequence is aligned with any other sequence so as to correspond as much as possible, and the aligned sequences are analyzed by using an algorithm commonly used in the art. Alignment methods for sequence comparison are known in the art.

Another aspect provides isolated nucleic acid encoding the antibody or the antigen-binding fragment thereof.

The term "nucleic acid", used herein, comprehensively refers to include DNA and RNA molecules, and a "nucleotide", which is a basic structural unit in nucleic acid, includes not only natural nucleotides but also analogues in which sugar or base sites are modified. The sequence of nucleic acid of an aspect encoding the heavy chain and light chain variable regions may be modified. The modification includes additions, deletions, or non-conservative or conservative substitutions of nucleotides.

The nucleic acid is also interpreted to include a nucleotide sequence that exhibits substantial identity to the nucleotide sequence of the nucleic acid. The substantial identity refers to a nucleotide sequence showing homology of at least 80%, more preferably homology of at least 90%, and the most preferably homology of at least 95%, when the nucleotide sequence according to an aspect is aligned with any other sequence so as to correspond as much as possible, and the aligned sequences are analyzed by using an algorithm commonly used in the art.

Still another aspect provides a vector including the isolated nucleic acid.

The vector may be obtained by using standard molecular biology techniques (for example, PCR amplification or cDNA cloning using a hybridoma expressing the antibody of interest) by obtaining DNA encoding a partial or full-length light chain and heavy chain, in order to express the antibody or the antibody fragment thereof in suitable host cells, and the vector may include necessary regulatory elements operably linked so that the DNA (gene) insert may be expressed. "Operably linked" refers to a functional linkage of a expression regulatory sequence of nucleic acid with a nucleic acid sequence encoding a protein or RNA of interest, and refers to a linkage that allows expression of a gene by the expression regulatory sequence.

The term "expression regulatory sequence (expression control sequence)" refers to a DNA sequence that regulates expression of an operably linked DNA sequence in a specific host cell. Such a regulatory sequence includes a promoter for executing transcription, any operator sequence for regulating transcription, a sequence encoding a suitable mRNA ribosome binding site, a sequence for regulating transcription and termination of translation, an initiation codon, a stop codon, a polyadenylation signal, an enhancer, etc. A person skilled in the art may be able to recognize that a design of the expression vector may change by selecting a different regulating sequence according to factors such as selection of host cells to be transformed, an expression level of the protein, and the like.

The vector is not particularly limited in its type as long as it is a vector commonly used in the field of cloning and antibody production, and examples thereof include, but are not limited to, plasmid vectors, cosmid vectors, bacteriophage vectors, and viral vectors. The plasm ids include *E. coli*-derived plasm ids (pBR322, pBR325, pUC118, and pUC119, pET-21b(+)), *Bacillus subtilis*-derived plasm ids (pUB110, and pTP5), and yeast-derived plasmids (YEp13, YEp24, and YCp50), etc., and for the viruses, animal viruses such as retroviruses, adenoviruses, or vaccinia viruses, insect viruses such as baculovirus, and the like may be used. A pComb3-type vector commonly used for phage display may be used, or a vector commonly used for protein expression in mammalian cells, such as pcDNA or pVITRO, may be used to express antibodies in mammalian cells.

Still another aspect provides isolated host cells transformed by the vector.

The term "transformation", used herein, refers to a molecular biological technique that changes genetic traits of a cell by which a piece of DNA chain or a plasm id having a foreign gene of a different kind from that of the original cell is introduced into cells, and binds to DNA existing in the original cell. The vector is transfected into host cells. A variety of techniques commonly used to introduce exogenous nucleic acid (DNA or RNA) into prokaryotic or eukaryotic host cells for transfection, such as electrophoresis, calcium phosphate precipitation, DEAE-dextran transfection, lipofection, or the like may be used.

The antibody or the antigen-binding fragment thereof according to an aspect may be expressed in eukaryotic cells, preferably mammalian host cells, considering the applicability to microorganisms such as bacteria (*E. coli*) or yeast, or mammalian cells. The mammalian host cell may be, for example, any one selected from the group consisting of Chinese hamster ovary (CHO) cells, NSO myeloma cells, COS cells, SP2 cells, F2N cells, HEK293 cells, and antibody-producing hybridoma cells, but is not limited thereto.

Still another aspect provides a method of preparing anti-mesothelin antibodies, including culturing the isolated host cells and expressing the antibodies.

The method may include transforming host cells for producing the antibodies or the antigen-binding fragments thereof according to an aspect with vectors operably linked to DNA encoding the antibody or the antigen-binding fragment thereof. The selected host cells and types of recombinant expression vectors are as described above, and the process may be carried out by selecting an appropriate transformation method. When the recombinant expression vectors encoding the antibody gene are introduced into mammalian host cells, antibodies may be prepared by culturing the host cells for a period of time sufficient to allow expression of the antibodies in the host cells, or more preferably for a period of time sufficient to allow secretion of the antibodies into the culture medium in which the host cells are cultured.

In addition, the method may additionally include culturing the transformed isolated host cells to produce polypeptides of the antibody or antigen-binding fragment thereof according to an aspect from the recombinant expression vectors introduced into the host cells. It is possible to appropriately select the medium composition, culture conditions, and culture time for culturing the selected host cells, and antibody molecules produced from the host cells may be allowed to be accumulated in the cytoplasm, secreted outside the cell or into the culture medium by an appropriate signal sequence, targeted to the periplasm, or the like. In addition, in order for the antibody according to an aspect to maintain the binding specificity for mesothelin, the antibody protein may be refolded to have a functional structure by using a method known in the art. In addition, when antibodies in a form of IgG are produced, the heavy chains and the light chains may be expressed in separate cells and prepared to construct complete antibodies by contacting the heavy chains and the light chains in a separate process, or the the heavy chains and the light chains may be expressed in the same cell to allow formation of complete antibodies inside the cell.

In addition, the method may additionally include a process of obtaining the antibodies or antigen-binding fragments thereof produced in the isolated host cells. The method of obtaining may be appropriately selected and adjusted, in consideration of characteristics of the polypeptide of the antibodies or antigen-binding fragments thereof produced in the host cells, characteristics of the host cells, mode of expression, or whether or not the polypeptide is targeted. For example, the antibodies or antigen-binding fragments thereof secreted into the culture medium may be recovered by a method such as obtaining the medium in which host cells are cultured and centrifuging to remove impurities, and when necessary, the cells may be lysed in a range that does not affect the functional structure of the antibodies or antigen-binding fragments thereof in order to release to the outside of the cell and recover the antibodies present in specific organelles or cytoplasm of the cell.

The obtained antibodies may be further subjected to a process of further removing impurities and concentrating through a method such as chromatography, filtration through a filter, or dialysis. Isolation or purification of the obtained antibodies may be performed by isolation and purification methods commonly used for proteins, such as chromatography. The chromatography may include, for example, affinity chromatography including a protein A column, protein G column, or protein L column, ion exchange chromatography, or hydrophobic chromatography. In addition to the above chromatography, antibodies may be isolated and purified by further combining filtration, ultrafiltration, salting out, dialysis and the like.

Still another aspect provides a chimeric antigen receptor including an antigen-binding domain, a hinge domain, a transmembrane domain, and an intracellular signaling domain.

The chimeric antigen receptor is characterized by specifically binding to mesothelin, and thus, includes an antigen-binding domain specifically binding to mesothelin.

The antigen-binding domain may include a heavy chain CDR1 including an amino acid sequence consisting of SEQ ID NO: 1; a heavy chain CDR2 including an amino acid sequence consisting of SEQ ID NO: 2; a heavy chain CDR3 including an amino acid sequence consisting of SEQ ID NO: 3; a light chain CDR1 including an amino acid sequence consisting of SEQ ID NO: 4; a light chain CDR2 including an amino acid sequence consisting of SEQ ID NO: 5; and a light chain CDR3 including an amino acid sequence consisting of SEQ ID NO: 6, and since the included is the same as in the anti-mesothelin antibody or antigen-binding fragment thereof according to an aspect, redundant descriptions will be omitted.

The term "chimeric antigen receptor (CAR)", used herein, refers to one forming a structure of a chimeric antigen receptor including an antigen-binding (recognizing) domain, a transmembrane domain, and an intracellular signaling domain.

In an embodiment, the antigen-binding fragment may be a single chain variable fragment (scFv).

The hinge domain, the transmembrane domain, and the intracellular signaling domain included in the chimeric antigen receptor are well known in the art.

The hinge domain is a domain connecting the anti-mesothelin antibody or antigen-binding fragment thereof with the transmembrane domain, and is also called a spacer, and has a purpose of extending an antigen-binding domain from a membrane of a T cell. The hinge domain may be a CD8 hinge domain, an IgG1 hinge domain, an IgG4 hinge domain, a CD28 extracellular region, a killer immunoglobulin-like receptor (KIR) extracellular region, and a combination thereof, but is not limited thereto, and a hinge domain commonly used in the art may be used.

The transmembrane domain serves as a support for the chimeric antigen receptor molecule and at the same time, may connect the hinge domain and the intracellular signaling domain. The transmembrane domain may penetrate the cell membrane of a cell, in order that the anti-mesothelin antibodies or antigen-binding fragments thereof of the chimeric antigen receptor are located on the cell surface, and the intracellular signaling domain is located inside the cell. The transmembrane domain may be a transmembrane domain of CD3zeta (CD3z), CD4, CD8, CD28, or KIR protein, preferably a transmembrane domain of CD8 or CD28 may be used, but any transmembrane domain commonly used for preparing a chimeric antigen receptor may be used without limitation.

The intracellular signaling domain serves to receive signals transmitted by the anti-mesothelin antibodies or antigen-binding fragments thereof and deliver it into the cell to which the chimeric antigen receptor is bound. The intracellular signaling domain is not particularly limited in its type, as long as it is a part that transmits a signal that may lead to T cell activation, when an antibody binds to an antigen-binding site present outside the cell, and various types of intracellular signaling domains may be used. The intracellular signaling domain may be, for example, an immunoreceptor tyrosine-based activation motif or ITAM, and the ITAM may include what is derived from CD3zeta, FcR gamma, FcR beta, CD3 gamma, CD3 delta, CD3 epsilon, CDS, CD22, CD79a, CD79b, CD66d, or FcεRIγ, but is not limited thereto.

In addition, the chimeric antigen receptor according to an aspect may further include a costimulatory domain together with an intracellular signaling domain.

The costimulatory domain refers to a part that serves to transmit a signal to a T cell in addition to signals transmitted by the intracellular signaling domain, and refers to an intracellular portion of a chimeric antigen receptor, including an intracellular domain of a costimulatory molecule.

The costimulatory molecule is a cell surface molecule, and refers to a molecule required to bring about a sufficient response of lymphocytes to an antigen, and may be, for example, CD27, CD28, 4-1BB, OX40, CD30, CD40, PD-1, ICOS, lymphocyte function-associated antigen-1 (LFA-1), CD2, CD7, LIGHT, NKG2C, or B7-H3, but is not limited thereto. The costimulatory domain may be an intracellular portion of a molecule selected from the group consisting of the above-mentioned costimulatory molecules and combinations thereof.

Each domain of the chimeric antigen receptor, including the transmembrane domain, and the intracellular signaling domain, may optionally be linked by a short oligopeptide or a polypeptide linker. The linker is not particularly limited in length, and any linker known in the art may be used, as long as it may induce T cell activation through the intracellular domain when an antigen is bound to an antibody located outside the cell.

In addition, the chimeric antigen receptor may include modified forms of the antibodies and domains as described above. In this regard, the modification may be performed by substituting, deleting, or adding one or more amino acids in an amino acid sequence of the wild-type antibody and domains without modifying the function of the antibody and domains. Typically, the substitution may be with alanine, or performed by a conservative amino acid substitution that does not affect the charge, polarity, or hydrophobicity of the entire protein.

Still another aspect provides a polynucleotide encoding the chimeric antigen receptor.

In consideration of degeneracy of codons, and preferred codons in an organism, in which the antigen receptor is to be expressed, the polynucleotide may have various modifications in the coding region, within a range that an amino acid sequence of the antigen receptor expressed from the coding region is not changed, and various modifications may also be made in parts other than the coding region, within a range that does not affect the gene expression, and those skilled in the art will be able to understand that such modified genes are also included within the scope of the present disclosure. That is, the polynucleotide according to an aspect may be mutated by substitution, deletion, insertion, or a combination thereof of at least one nucleic acid base, within a range that a protein having an activity equivalent to the unmodified/original protein is encoded, and the mutated polynucleotides are also included in the scope of the present disclosure.

Still another aspect provides a vector including the polynucleotide and isolated cells transformed with the vector.

Various vectors known in the art may be used as the vector, and according to the type of the host cells for producing the antigen receptors, expression regulatory sequences such as a promoter, a terminator, an enhancer, etc, and a sequence for membrane targeting or secretion, etc. may be appropriately selected and combined in various ways depending on the purpose. The vector of the present disclosure includes, but is not limited to, a plasm id vector, a cosmid vector, a bacteriophage vector, and a viral vector. An appropriate vector includes expression regulatory elements such as a promoter, an operator, an initiation codon, a stop codon, a polyadenylation signal, and an enhancer, as well as a signal sequence or a leader sequence for membrane targeting or secretion, and may be prepared in various ways according to a purpose.

In addition, cells may be transformed by introducing the vector into the cells, and the isolated cells may be, but are not limited to, T cells, NK cells, NKT cells, or gamma delta (γδ) T cells. The isolated cells may be obtained or prepared from bone marrow, peripheral blood, peripheral blood mononuclear cells, or umbilical cord blood.

Still another aspect provides a pharmaceutical composition including the isolated cells; medical use of the isolated cells; and a method of preventing or treating cancer, including administering the isolated cells in a therapeutically effective amount to a subject.

Since the pharmaceutical composition uses the above-described isolated cells, descriptions of the common content between the two are omitted in order to avoid excessive complexity of the present specification.

The pharmaceutical composition or medical use may be for preventing or treating cancer.

The term "prevention", used herein, refers to all acts of suppressing, or delaying an onset of a cancer (tumor), by administering the pharmaceutical composition according to the present disclosure.

The term "treatment", used herein, refers to all acts of improving or advantageously altering symptoms of a cancer (tumor), by administering the pharmaceutical composition according to the present disclosure.

The term "subject", used herein, refers to a subject in need of treatment of a disease, and more specifically, refers to a mammal such as a human, or a non-human primate, a rodent (rat, mouse, guinea pig, etc.), a mouse, a dog, a cat, a horse, a cow, sheep, a pig, a goat, a camel, an antelope, etc.

The term "cancer", used herein, is a generic term for diseases caused by cells with: aggressive characteristics in which the cells divide and grow beyond normal growth limits; invasive characteristics in which the cells infiltrate into surrounding tissues; and metastatic characteristics in which the cells spread to other parts of the body and outside the body. In the present specification, the cancer is used in the same sense as a malignant tumor, and may preferably be a mesothelin-positive or mesothelin-overexpressing cancer.

The cancer may preferably be a solid cancer, for example, more preferably a mesothelin-positive or mesothelin-overexpressing solid cancer. For example, the solid cancer may be at least one selected from the group consisting of esophageal cancer, breast cancer, triple-negative breast cancer (TNBC), gastric cancer, cholangiocarcinoma, pancreatic cancer, colon colon cancer, lung cancer, thymic carcinoma, mesothelioma, ovarian cancer, endometrial cancer, cervical cancer, uterine serous carcinoma (USC), non-small cell lung cancer, and pediatric acute myeloid leukemia (AML), but is not limited thereto.

The pharmaceutical composition may include the cells of an aspect, which are an active ingredient, in an amount of 10 wt % to 95 wt %, with respect to a total weight of the pharmaceutical composition. In addition, the pharmaceutical composition of the present disclosure may additionally contain one or more active ingredients exhibiting the same or similar function, in addition to the active ingredient.

A dosage of the cells may be adjusted according to various factors, including a type of the disease, severity of the disease, types and contents of active ingredients and other ingredients contained in the pharmaceutical composition, a type of the formulation, age, weight, general health condition, sex, and diet of the patient, administration time, a route of administration, duration of treatment, and drugs used concurrently. However, for a desired effect, an effective amount of cells included in the pharmaceutical composition according to the present disclosure may be $1\times10^5$ cells/kg to $1\times10^{11}$ cells/kg. In this regard, the pharmaceutical composition may be administered once a day, or may be divided and administered several times. An effective amount of the cells or pharmaceutical composition presented herein may be determined empirically without undue experimentation.

The pharmaceutical composition may be a medicine having a formulation suitable for a purpose, and is prepared according to a commonly used method in the pharmaceutical field. In addition, the composition may be administered after being formulated into a unit dosage form suitable for administration into the body of a patient, according to a commonly used method in the pharmaceutical field. The pharmaceutical formulation may further include, in addition to the active ingredient, one or more pharmaceutically acceptable inert carriers in the art, for example, in the case of an injection, preservatives, analgesics, solubilizers, stabilizers, etc., and in the case of formulations for topical administration, a base, an excipient, a lubricant, a preservative, etc.

In addition, the cells or pharmaceutical compositions including the same may be administered to a subject by various methods known in the art, for example, by intraperitoneal administration, intravenous administration, intramuscular administration, subcutaneous administration, intradermal administration, oral administration, topical administration, intranasal administration, intrapulmonary administration, intrarectal administration, etc., but the administration method is not limited thereto.

Advantageous Effects

An anti-mesothelin chimeric antigen receptor according to an aspect exhibits a specific binding ability for mesothelin, and thus, may be useful for preventing or treating a mesothelin-overexpressing cancer.

BRIEF DESCRIPTION OF THE DRAWINGS

FIG. 2 shows results of solid phase panning, in which FIG. 2A is a diagram showing phage output titers according to panning rounds, and FIG. 2B is a diagram showing elution titer ratios (B), according to panning rounds.

MODE FOR INVENTION

Hereinafter, an aspect will be described in more detail through examples. However, these examples are intended to illustrate an aspect by way of example, and the scope of the aspect is not limited to these examples, and an example of an aspect provides a more complete description of the aspect to those skilled in the art.

Example 1: Phage Display Antibody Library Panning

Figure 1:
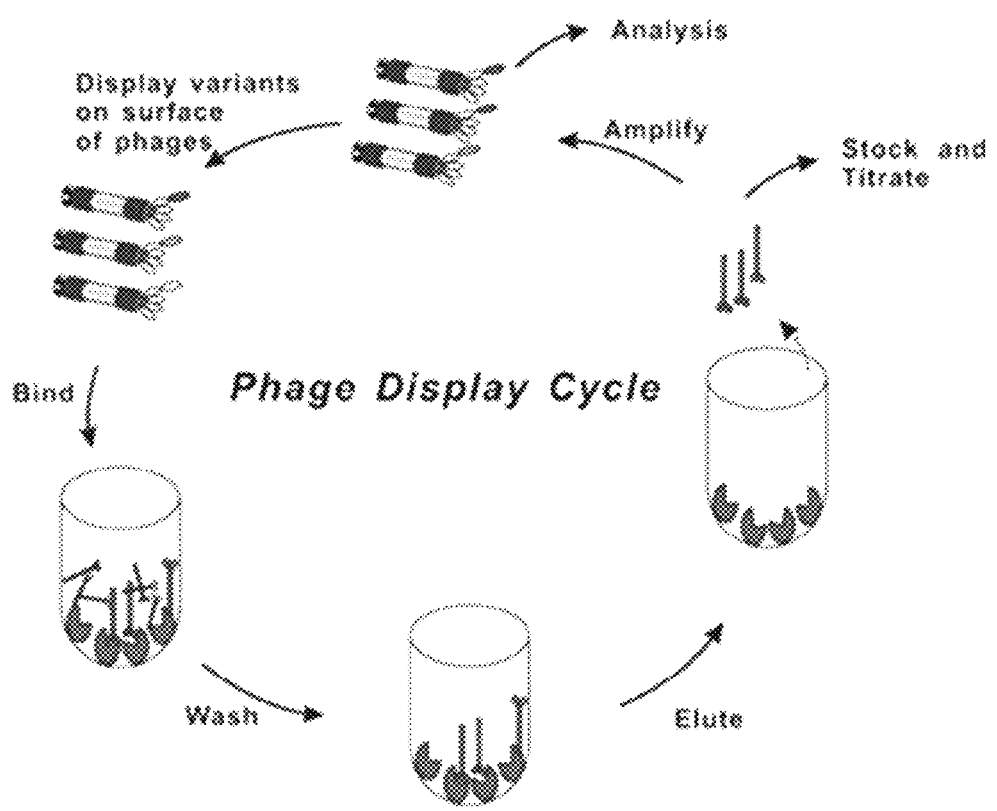
FIG. 1 is a diagram schematically illustrating a process of antibody screening through phage display antibody library panning.

In order to select an antibody that binds to mesothelin (MSLN), which is a target antigen, phage panning for MSLN (Acro Biosystems) was performed up to 4 rounds by using the KBIO human synthetic scFv phage display library KscFv-I, according to the phage panning protocol established by the New Drug Development Support Center of the Osong Advanced Medical Industry Promotion Foundation. The phage display antibody library panning process is schematically shown in FIG. 1.

Panning was performed in two ways (solid and bead) depending on a method of immobilizing the antigen. For solid phase panning, 1 mL of human mesothelin proteins (in PBS, 1st round: 10 μg/mL, 2nd round: 5 μg/mL, 3rd round: 2.5 μg/mL, and 4th round: 1.25 μg/mL) were immobilized on an immunotube, and $1.3 \times 10^{13}$ c.f.u. of the phage library blocked with 5 mL of PBS (MPBS) including 5% skim milk was added to the immunotube, and then bound at 37° C. for 1.5 hours. Then, unbound phages were removed by washing with 5 mL of PBS-Tween20 (0.05%) (PBS-T) (1st round: washed 3 times, 2nd to 4th rounds: washed 5 times). Here, 1 mL of 100 mM trimethylamine (TEA) was added to the tube and reacted at room temperature for 10 minutes to elute the bound phages, and the eluted phages were moved to a 50 mL falcon tube, and mixed well with 0.5 mL of 1 M Tris-HCl (pH 7.4) to neutralize. The eluted phages were infected into 8.5 mL of mid-log phase *E. coli* TG1 (OD600=0.5 to 0.8). Some of the transfected *E. coli* TG1 were subjected to extraction of plasmid DNA for sequence confirmation, and some were subjected to antibody screening through phage ELISA. The results are shown in FIGS. 2A and 2B.

As a result, as shown in FIG. 2, the samples started to concentrate from the third round of solid phase panning, and the yield titer for the MSLN antigen showed a large difference of about 53.4 times (third round) and 1061.6 times (fourth round) greater values compared to the PBS control group.

Example 2: Selection of Positive Clones Through Phage-Specific ELISA

In order to select clones that specifically bind to the MSLN antigen among the phages obtained by the phage panning of Example 1, a monoclonal phage ELISA was performed for 470 (94 colonies×5 plates) clones obtained from the third round of panning by using an immunotube. Specifically, 30 μL per well of 1 μg/mL human MSLN proteins (antigen) was added to a 96-half-well ELISA plate, followed by incubation at 4° C. overnight for coating. As a negative control group, 30 μL per well of PBS was added to another plate and incubated overnight at 4° C. The next day, the contents of the plate were removed and the plate was blocked with 150 μL of 5% MPBS for 1 hour at room temperature. Then, the contents of the plate were removed, and 30 μL of phages (~10" c.f.u.) was added and incubated for 1.5 hours at room temperature. For a negative control group, 30 μL of PBS was added instead of the phages. The plate was washed 4 times with a PBS-T (PBS-0.05% Tween 20) solution, anti-M13-HRP (diluted to 1:5,000 in PBS) was added and incubated at 37° C. for 1 hour. The plate was washed 4 times with the PBS-T solution, and 30 μL of TMB substrate reagent was added to each well and incubated for 8 minutes at room temperature to induce a color reaction. After stopping the color reaction by adding 30 μL of 2 N $H_2SO_4$ per well, absorbance (O.D.) at 450 nm was measured.

As a result, a total of 105 positive clones were secured in the third round when screening was performed by respectively setting the absorbance cut-off to 0.7 or higher, or 0.5 or higher, for the MSLN antigen. Additionally, monoclonal phage ELISA was performed in the same manner for the clones obtained in the fourth round of panning by using an immunotube. As a result of performing phage ELISA for 282 (94 colonies×3 plates) clones obtained in the 4th round of panning, and screening by setting each of the absorbance cut-off to 0.7 or higher, a total of 15 positive clones were secured (Tables 1 to 3).

TABLE 1

| Panning at 3rd round (Round 3) | Absorbance (450 nm) | Number of positive clones | Number of unique clones |
| --- | --- | --- | --- |
| 3R-1 | >0.7 | 35 | 6 |
| 3R-2 | >0.7 | 4 | 1 |
| 3R-3 | >0.7 | 8 | 2 |
| 3R-4 | >0.5 | 34 | 9 |
| 3R-5 | >0.5 | 24 | 2 |
| Total sum | | 105 | 20 |

TABLE 2

| Panning at 4th round (Round 4) | Absorbance (450 nm) | Number of positive clones | Number of unique clones |
| --- | --- | --- | --- |
| 4R-1 | >0.7 | 6 | 1 |
| 4R-2 | >0.7 | 2 | 0 |
| 4R-3 | >0.7 | 7 | 1 |
| Total sum | | 15 | 2 |

TABLE 3

| Panning at 3rd and 4th rounds | Total sum |
| --- | --- |
| Number of positive clones | 120 |
| Number of unique clones | 22 |

Example 3: Sequence Analysis and ELISA for Screening Anti-MSLN Antibody Fragment Candidates After recovering phages from a total of 120 positive clones selected in Example 2, a DNA sequence analysis was proceeded, and the sequences were aligned and grouped according to the Kabat numbering system. As a result, 22 unique clones for MSLN antigens with different CDR sequences were selected. In order to confirm specific binding of the 22 clones to the MSLN antigen, each phage was purified and the phage titer was equalized (3.3E+11 pfu/well), and then the phages were compared through ELISA. As a negative control, a TLR4 antigen conjugated to a histidine tag (His tag) was used in the same way as with MSLN. The results are shown in FIG. 3.

Figure 3:
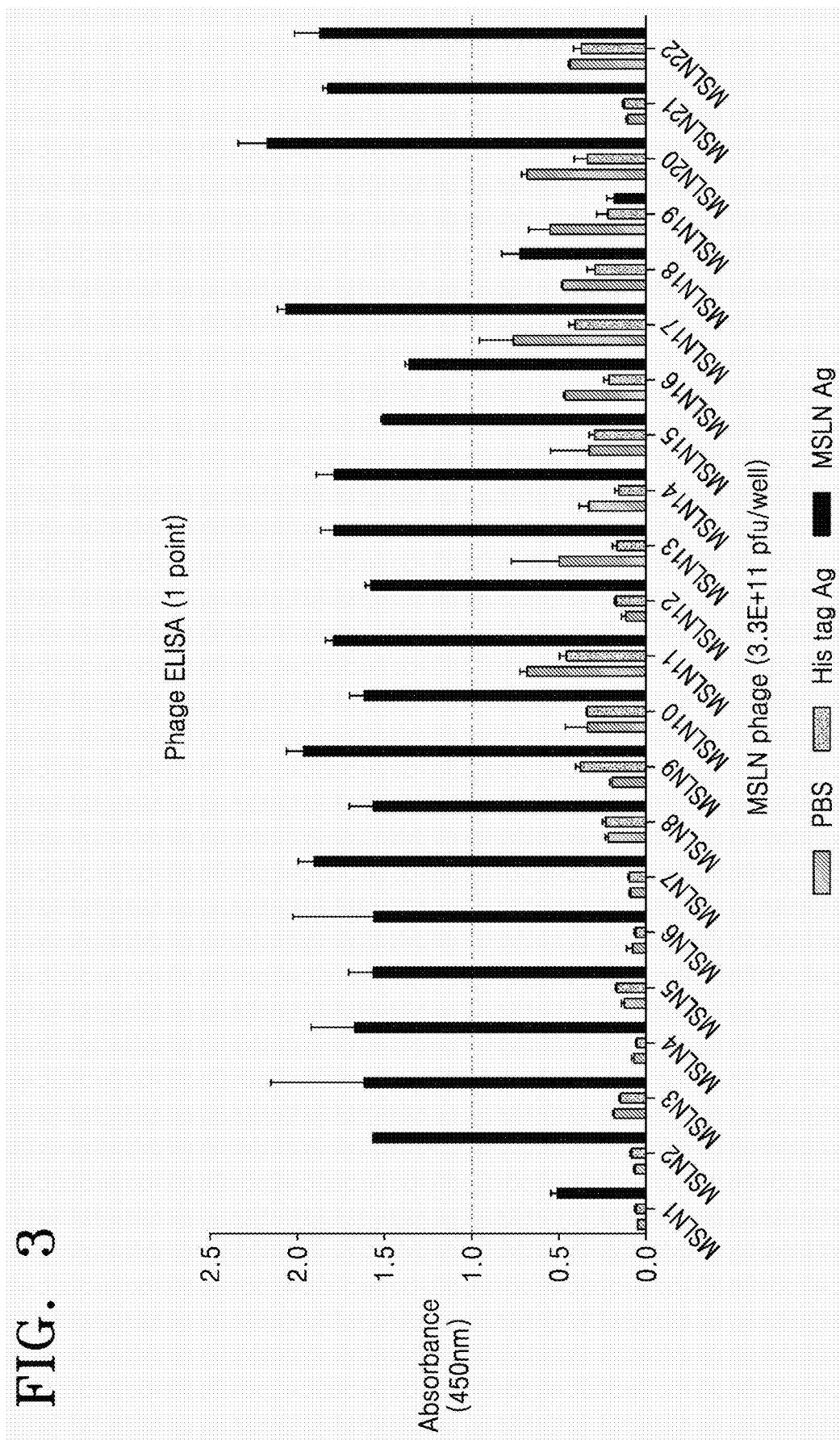
FIG. 3 is a diagram showing results of a comparative analysis of specific binding for an MSLN antigen of clones obtained through phage ELISA.

As shown in FIG. 3, it was confirmed that 19 clones excluding MSLN1, MSLN18, and MSLN19 among the 22 clones specifically bind to the MSLN antigen.

Example 4: Confirmation of Binding Ability by Using Mesothelin-Overexpressing Cell Lines In order to know whether the 19 types of phage clones selected in Example 3 bind to mesothelin present in the actual cell membrane, a flow cytometry analysis was performed by using a pancreatic cancer cell line AsPC-1, which is a mesothelin-overexpressing cell line, and a human chronic myeloid leukemia cell line K562 as a control group.

Specifically, K562 and AsPC-1 cells were prepared to be $10^6$ cells/well and washed with 300 μL of PBS. The cells were blocked with 300 μL of 4% MPBS at 4° C. for 30 minutes, and at the same time, the phage clones (10' 2/well) were also blocked for 1 hour at room temperature, and then the phages and cells were incubated together at 4° C. for 2 hours. After washing the cells with PBS, the cells were treated with 1 μg/mL of anti-M13-FITC and incubated at 4° C. for 1 hour. After washing the cells with PBS, the cells were resuspended in PBS and the results were analyzed by using a flow cytometer (BD biosciences). The results are shown in FIGS. 4 and 5.

Figure 4:
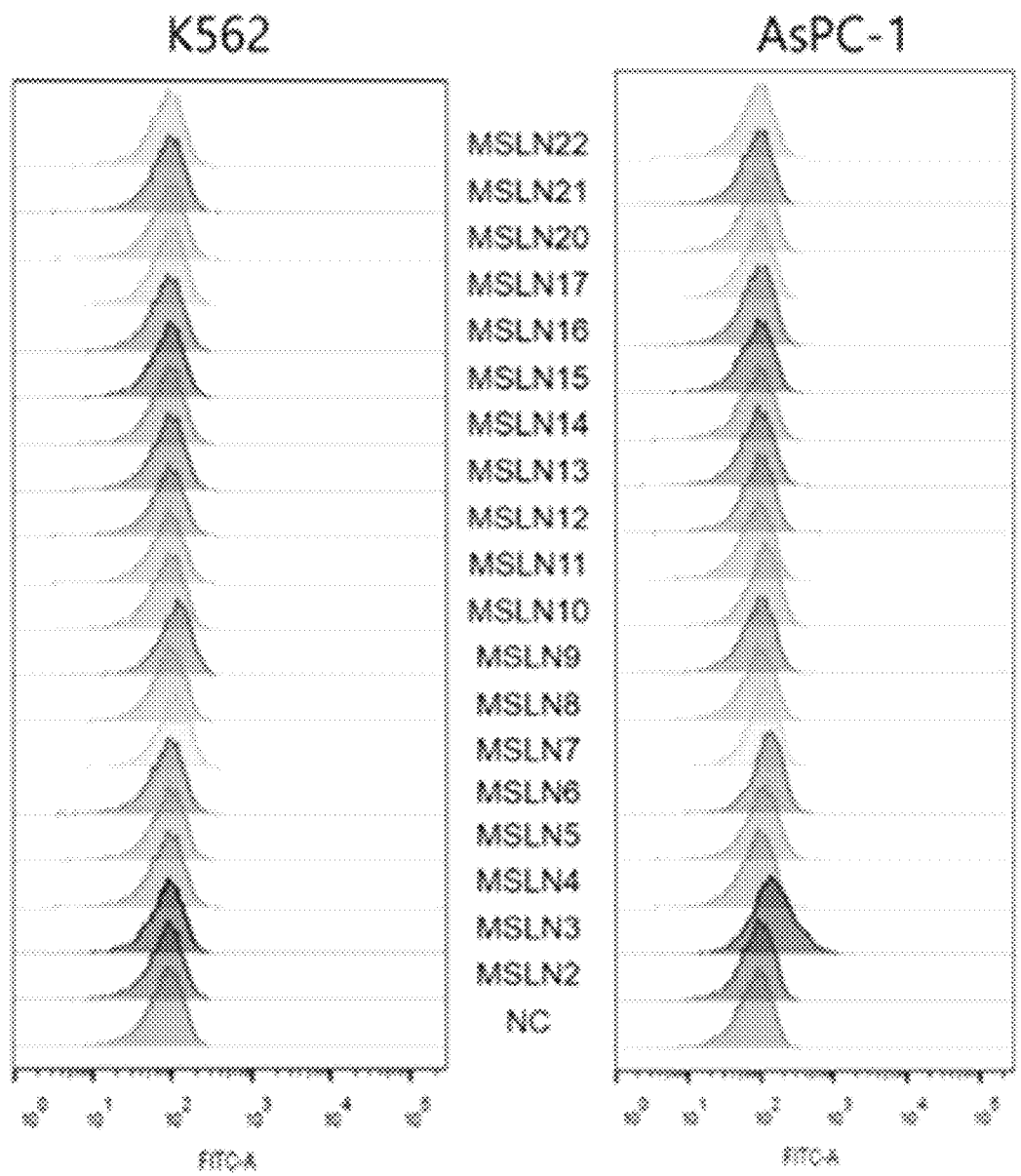
FIG. 4 is a diagram showing results of confirming through flow cytometry whether clones selected by using a mesothelin-overexpressing cell line bind to mesothelin present in actual cell membranes.

As shown in FIG. 4, it was confirmed that MSLN3, MSLN6, and MSLN10 exhibited a relative peak shift value of 3.0% or more in the pancreatic cancer cell line AsPC-1. In the K562 cell line, which is a control group, no significant peak shift was observed. From the above results, it was found that among the 19 clones, MSLN3, MSLN6 and MSLN10 showed high binding affinity to mesothelin present in the actual cell membrane.

Figure 5:
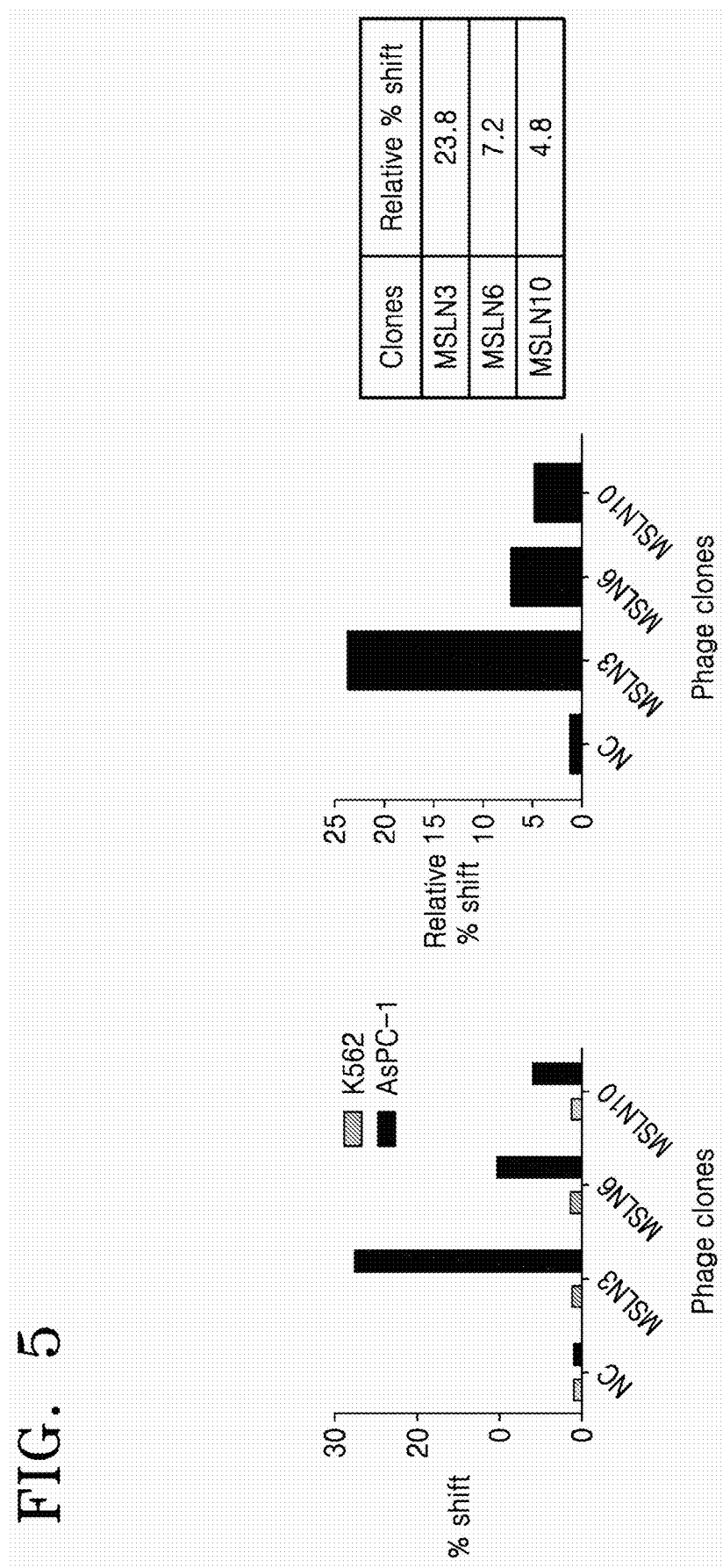
FIG. 5 is a diagram showing binding specificity for mesothelin of clones selected by using a mesothelin-overexpressing cell line, with relative peak shift values.

In addition, as shown in FIG. 5, as a result of quantifying flow cytometry results, it was confirmed that MSLN3, MSLN6, and MSLN10 showed relative peak shift values of 23.8%, 7.2%, and 4.8%, respectively, compared to the K562 cells, which is the control group. Through the above results, all three clones were confirmed to specifically bind to the cell line in which mesothelin is overexpressed, and finally selected as clones for producing anti-MSLN antibody fragments.

Example 5: Anti-MSLN Antibody Fragment Production and Purification

Figure 6:
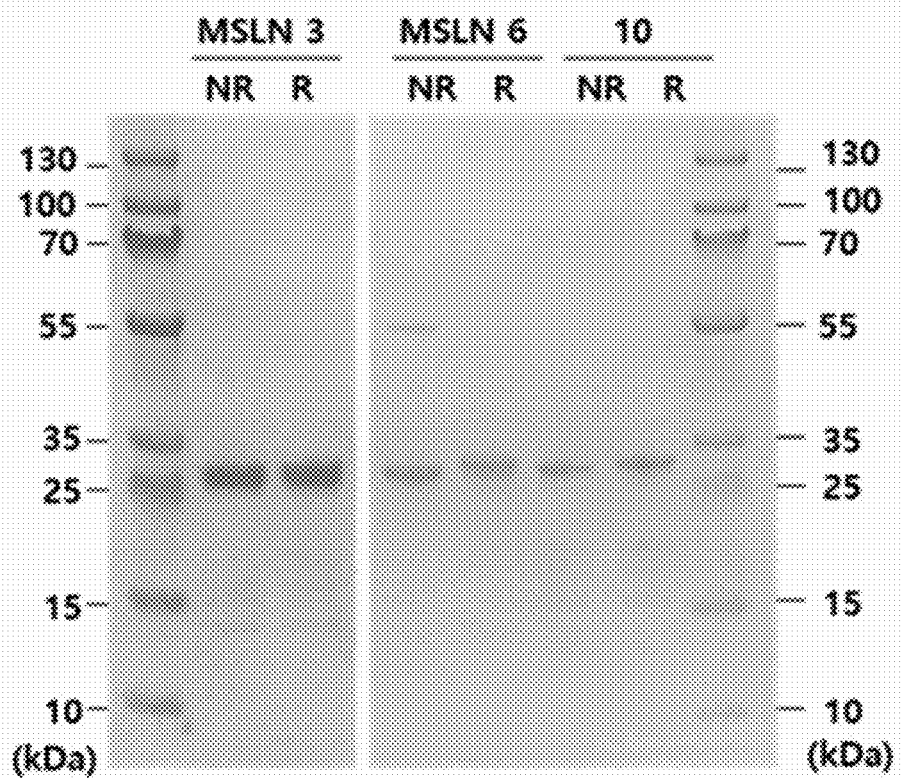
FIG. 6 is a diagram showing results of SDS-PAGE analyses of purified anti-MSLN-scFv antibodies (loading 2 μg of each protein). NR: Non-reducing condition, R: Reducing condition (100° C., 10 minutes).

By using the three clones selected in Example 4, Top10F' competent *E. coli*, a strain expressing antibody fragments, was transformed. Then, each of the *E. coli* strains transformed with the three clones was cultured in 200 mL of TB medium, protein expression was induced with IPTG (final concentration: 0.5 mM), and the *E. coli* strains were cultured overnight at 30° C. The cells were obtained by centrifuging the culture medium, and after securing water-soluble proteins through periplasmic extraction, anti-MSLN-scFv antibodies were purified through affinity chromatography by using protein L resin. The purified antibody proteins were analyzed by SDS-PAGE, and the results are shown in FIG. 6.

Example 6: Analysis of Affinity of Anti-MSLN Antibodies for Antigens and Selection of Clones to be Used as Final Anti-MSLN Chimeric Antigen Receptors Affinity of each antibody to the MSLN antigen was compared and analyzed through ELISA by using the three types of anti-MSLN antibody proteins prepared in Example 5 above. Specifically, 30 µL of human mesothelin proteins were coated on a MaxiSorb ELISA plate (Nunc) to a concentration of 1 µg/mL per well, and incubated overnight at 4° C. The contents of the plate were removed and the plate was blocked with 300 µL of 5% MPBS for 1 hour at room temperature. The purified antibodies were serially diluted in PBS, and added to each well by 30 µL and incubated for 2 hours at room temperature. For a negative control group, 60 µL of PBS was added instead of the purified antibodies and incubated at 37° C. for 2 hours.

The plate was washed 4 times with a PBS-T (PBS-0.05% Tween 20) solution, 30 µL of anti-StrepMAB HRP (diluted to 1:5,000 in PBS) was added and incubated at room temperature for 1 hour. The plate was washed 4 times with the PBS-T solution, and 30 µL of TMB substrate reagent was added to each well and incubated for 8 minutes at room temperature to induce a color reaction. After stopping the color reaction by adding 30 µL of 2 N $H_2SO_4$ per well, absorbance (O.D.) at 450 nm was measured. The results are shown in FIG. 7.

Figure 7:
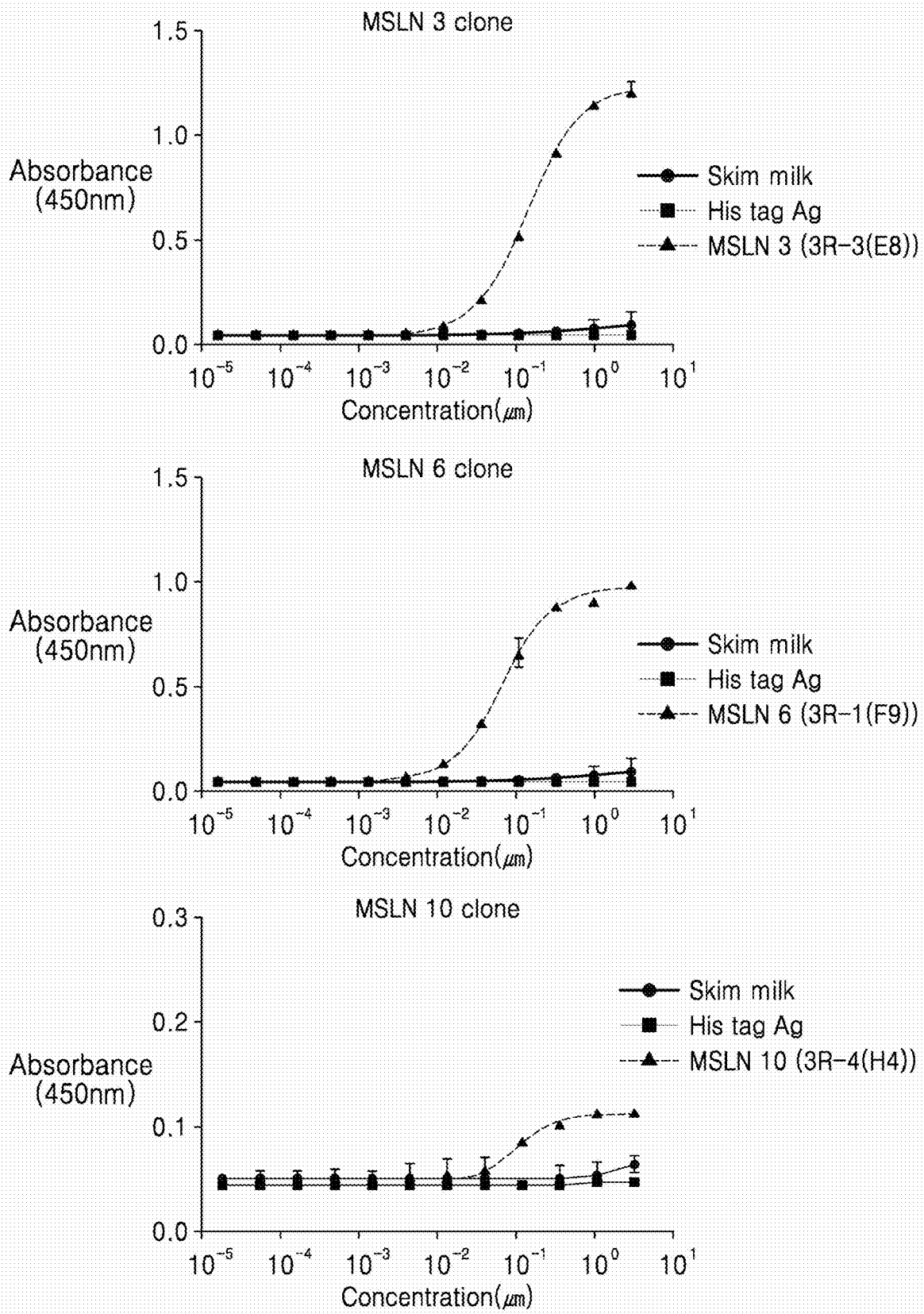
FIG. 7 is a diagram showing results of analyzing the affinity of anti-MSLN-scFv antibodies for an MSLN antigen through ELISA.

As shown in FIG. 7, $EC_{50}$ values of the three types of antibodies were 145 nM, 67 nM, and 91 nM for MSLN3, MSLN6, and MSLN10, respectively, confirming that MSLN3 showed the highest binding affinity among the three antibodies (see Table 4).

TABLE 4

| Ranking | MSLN clone | $R^2$ | $EC_{50}$ (nM) |
| --- | --- | --- | --- |
| 1 | 3 | 0.999 | 145 |
| 2 | 10 | 0.988 | 91 |
| 3 | 6 | 0.988 | 67 |

Accordingly, the MSLN3 was finally selected as a clone for producing anti-MSLN antibody fragments, and the amino acid sequence of MSLN3 was confirmed and shown in Table 5 below. Specifically, the heavy chain CDR1-3 amino acid sequences of MSLN3 are respectively shown in SEQ ID NOS: 1 to 3, the light chain CDR1-3 amino acid sequences are respectively shown in SEQ ID NOS: 4 to 6, and the heavy chain amino acid sequence and light chain amino acid sequence are respectively shown in SEQ ID NOS: 7 and 8.

TABLE 5

Heavy chain CDR1-3 and light chain CDR1-3 amino acid sequences of MSLN3 of MSLN3 clones

| Region | Amino acid sequence | SEQ ID NO: |
| --- | --- | --- |
| HCDR1 | DYAMS | 1 |
| HCDR2 | AISSSGGTTYYADSVKG | 2 |
| HCDR3 | EEEGEWREYFDV | 3 |
| LCDR1 | RASQSISSYLN | 4 |
| LCDR2 | ATSTLQS | 5 |
| LCDR3 | QQSYTFPYT | 6 |
| VH | EVQLVESGGGLVQPGGSLRLSCAASGFTFSDYAMSW VRQAPGKGLEWVSAISSSGGTTYYADSVKGRFTISR DNSKNTLYLQMNSLRAEDTAVYYCAKEEEGEWREYF DVWGQGTLVTVSS | 7 |
| VL | DIQMTQSPSSLSASVGDRVTITCRASQSISSYLNWY KQQKPGAPKLLIYATSTLQSGVPSRFSGSGSGTDFT LTISSLQPEDFATYYCQQSYTFPYTFGQGTKVEIK | 8 |

Example 7: Construction of Anti-MSLN Chimeric Antigen Receptor

An anti-MSLN chimeric antigen receptor was constructed (anti-MSLN-CAR) based on MSLN3, which showed high binding specificity with a cell line overexpressing mesothelin among the anti-MSLN antibody proteins prepared in Example 6.

7-1: Cloning of Anti-MSLN-CAR Lentiviral Vectors

The vector belongs to the 2nd generation CAR lentiviral vector (pLV lentiviral vector) system retained by the New Drug Development Support Center, and the system includes all of pMDLg/pRRE (addgene) encoding gag/pol, an envelope plasmid pRSV-Rev (addgene) encoding Rev proteins, and an envelope plasmid pMD2.G (addgene) encoding VSV-G proteins.

First, gene cloning was performed on the anti-MSLN scFv (antigen-binding domain) prepared in Example 6. Each anti-MSLN scFv of MSLN3 and lentiviral vectors were digested with XhoI (R0146S, NEB) and EcoRI (R0101, NEB) at 37° C. for 2 hours, subjected to agarose gel electrophoresis, and the identified products were purified by using the FavorPrep Gel/PCR purification Mini kit (Favorgen). Each purified anti-MSLN scFv (100 ng) and the vectors (50 ng) were reacted at a ratio of 2:1 at 16° C. for 16 hours for ligation, and then Stbl3 competent cells were transformed by the vectors, and then colonies were obtained. The colonies were taken and cultured in 5 mL of LB medium (ampicillin), and then plasmid DNA was obtained by using a DNA plasmid mini-prep method. The plasmid DNA was digested with XhoI and EcoRI to confirm whether each inserted anti-MSLN scFv was well cloned into the vector. Afterwards, sequencing was performed to finally confirm the DNA sequence.

Anti-MSLN-CAR was constructed by sequentially connecting to the anti-MSLN scFv, a CD8 hinge and a CD8 transmembrane (TM) as transmembrane regions, a cytoplasmic region of 4-1BB as a signaling domain, and an intracellular domain of CD3 zeta (CD3z) as a T cell activation domain. Specifically, anti-MSLN-CAR consists of a CD8 signal peptide (SP) (SEQ ID NO: 10), anti-MSLN3 scFv (SEQ ID NO: 11), a CD8 hinge region (SEQ ID NO: 12), a CD8 transmembrane region (SEQ ID NO: 13), a 4-1BB signaling domain (SEQ ID NO: 14), and a CD3 zeta signaling domain (SEQ ID NO: 15). Each of the above domains was sequentially linked by using each restriction enzyme, and specific nucleotide sequence information corresponding to each domain is summarized in Table 6 below.

TABLE 6

| Name | Nucleotide sequence (5'-3') | SEQ ID NO: |
|---|---|---|
| CD8 | ATGGCCTTACCAGTGACCGCCTTGCTCCTGCCGCTGGC CTTGCTGCTCCACGCCGCCAGGCCG | 10 |
| MSLN3 scFv | GAAGTACAGTTGGTCGAAAGTGGCGGTGGCCTCGTGCA ACCGGGTGGTTCACTGCGTCTGAGCTGCGCCGCCTCGG GTTTTACTTTCTCTGATTATGCAATGTCTTGGGTTCGT CAGGCGCCGGGCAAGGGTCTCGAATGGGTTTCAGCAAT CTCTTCTTCTGGTGGTACTACTTACTATGCCGATTCAG TGAAGGGTCGCTTTACCATTTCCCGTGACAACTCTAAG AATACTCTGTATCTGCAGATGAACTCGCTGCGTGCCGA AGACACGGCCGTCTATTATTGCGCCAAAGAAGAAGAAG CGTGAATGGCGTGAATACTTCGATGTTTGGGGTAGGGC ACTTTAGTGACCGTCTCATCGGGTGGAGGCGGTTCAGG CGGAGGTGGATCCGGCGGTGGCGGATCGGACATTCAAA TGACGCAGAGTCCCTCCTCACTGAGTGCTAGCGTGGGC GATCGTGTGACAATTACTTGTCGCGCTAGCCAGTCTAT CTCTTCTTACCTGAACTGGTATCAGCAGAAACCGGGCA AGGCGCCAAAATTGCTGATTTACGCAACTTCCACTCTG CAGTCTGGTGTACCGTCCCGTTTCTCTGGCAGCGGTTC TGGTACGGATTTTACCCTGACCATCTCAAGCCTCCAGC CTGAAGATTTTGCCACCTATTATTGTCAGCAATCTTAC ACTTTTCCGTACACGTTCGGGCAGGGAACTAAAGTGGA AATTAAAGCCAGCACC | 11 |
| CD8 hinge | ACCACGACGCCAGCGCCGCGACCACCAACACCGGCGCC CACCATGCGCTCGCAGCCCCTGTCCCTGCGCCCAGAGG CCGTGCGGCCAGCGGGGGGGCGCAGTGCACACGAGGG GGCTGGACTTCGCCTGTGAT | 12 |
| CD8 TM | ATCTACATCTGGGCGCCCTTGGCCGGGACTTGTGGGGT CCTTCTCCTGTCACTGGTTATCACCCTTTACTGC | 13 |
| 4-1BB | AAACGGGGCAGAAAGAAACTCCTGTATATATTCAAACA TACCATTATGAGACCAGTACAAACTACTCAAGAGGAAG ATGGCTGTAGCTGCCGATTTCCAGAAGAAGAAGAAGGA GGATGTGAACTG | 14 |
| CD3z | AGAGTGAAGTTCAGCAGGAGCGCAGACGCCCCCGCGTA CACAGCAGGGCCAGAACCAGCTCTATAACGAGCTCAAT CTAGGACGAAGAGAGGAGTACGATGTTTTGGACAAGAG ACGTGGCCGGGACCCTGAGATGGGGGGAAAGCCGAGAA GGAAGAACCCTCAGGAAGGCCTGTACAATGAACTGCAG AAAGATAAGATGGCGGAGGCCTACAGTGAGATTGGGAT GGAAAGGCGAGCGCCGGAGGGCAAGGGGCACGATGGCC TTTACCAGGGTCTCAGTACAGCCACCAAGGACACCTAC GACGCCCTTCACATGCAGGCCCTGCCCCCTCGC | 15 |

7-2: Production of Lentiviruses Loaded with Anti-MSLN-CAR

Figure 8:
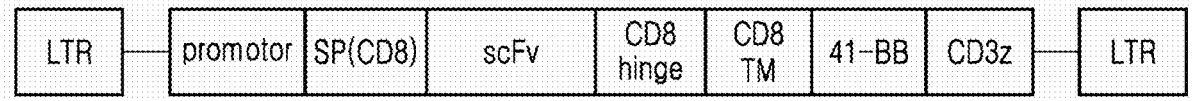
FIG. 8 is a schematic diagram of an anti-MSLN-CAR expression system according to an aspect, including an MSLN-specific antigen-binding domain.

Anti-MSLN-CAR lentiviruses were produced by introducing the recombinant vectors prepared in Example 7-1 into HEK293T cells. FIG. 8 shows a schematic diagram of an anti-MSLN-CAR expression system according to an aspect including an MSLN-specific antigen-binding domain. First, the day before DNA transfection, HEK293T cells were seeded in a 100 mm tissue culture dish at $6 \times 10^6$ cells/dish. The next day, when cell density reached 70% to 80%, the cells were transformed with MSLN-CAR-pLV, pMDLg/pRRE (addgene), pRSV-Rev (addgene), pMD2.G (addgene) (5.5 μg:3.5 μg:1.5 μg:2 μg), by using lipofectamine 3000 (Thermofisher) according to instructions of the reagent. CD19 (FMC63) was used as a control group. 4 hours after the transformation, the medium was replaced with DMEM medium including 3% FBS (Gibco), and after 48 hours, the viral culture medium was harvested. 10 mL of a 20% sucrose solution was put into a centrifugal separation tube, and 20 mL of the harvested viral culture medium was carefully placed thereon, and the centrifugal separation tube was mounted on a SW32T rotor, and ultra-high-speed centrifugation was performed at 25,000 rpm at 4° C. for 90 minutes. After the centrifugation, the supernatant was carefully discarded not to drop the viral pellet at the bottom of the tube, 400 μL of RPMI1640 medium (Gibco) was added, and the sample was incubated in the refrigerator for 16 hours, resuspend, and divided into 100 μL each, and stored at −80° C.

Example 8: Construction of Anti-MSLN-CAR-Introduced Cells 8-1: Lentiviral Transduction Anti-CD3 (1 μg/mL) and anti-CD28 (3 μg/mL) antibodies were prepared in 5 mL of DPBS to the designated concentrations, vortexed, and then coated on a 24-well plate at 500 μl/well and stored overnight in a refrigerator at 4° C. The next day, PBMC (primary human PBMC) was dissolved in 9 mL of T cell culture medium (10% FBS+RPMI1640+200 IU IL-2) and centrifuged at 1,500 rpm for 5 minutes. Thereafter, the supernatant was removed, and the remainder was resuspended in 1 mL of the culture medium, and the cells were counted, then the sample was diluted to $1 \times 10^6$ cells/mL, seeded in an antibody-coated 24-well plate, and cultured in a $CO_2$ incubator at 37° C. After 3 days, all the PBMC cells were harvested, and lentiviruses were adjusted to multiple of infection (MOI) of 5 in cells at a concentration of $5 \times 10^5$ cells/500 μL for lentiviral infection, and 10 μg/mL of protamine sulfate was added, and the sample was seeded in a new 24-well plate (a). The 24-well plate was centrifuged at 300 g and 32° C. for 90 minutes, and then placed in a $CO_2$ incubator at 37° C. and cultured (b). The next day, all T cells were harvested and processes (a) and (b) were performed once more. Then, all the T cells were harvested, centrifuged at 1,500 rpm for 5 minutes to remove the supernatant, and the T cells were resuspended in the culture medium and cultured again.

8-2: Confirmation of Expression of Anti-MSLN-CAR

Figure 9A:
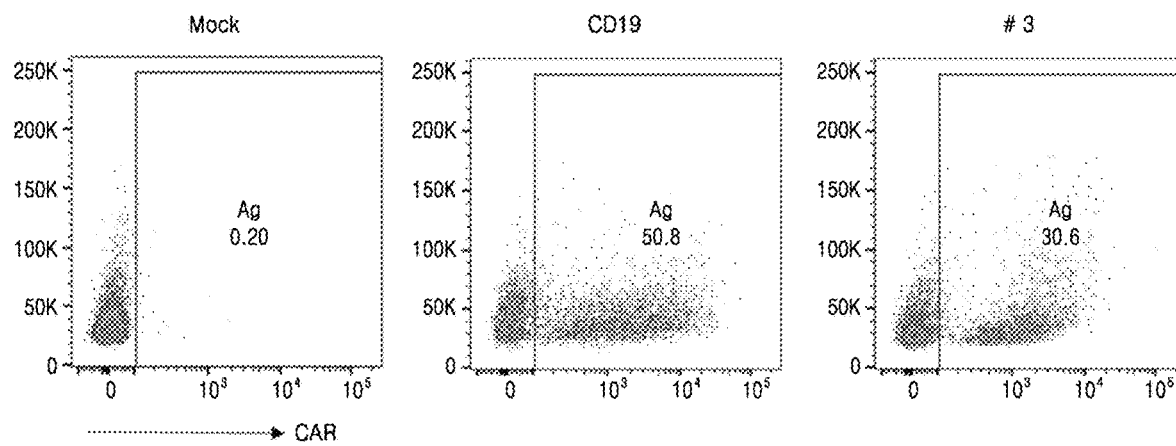
FIG. 9A is results of confirming expression of CAR in T cells into which anti-MSLN-CAR was introduced.
Figure 9B:
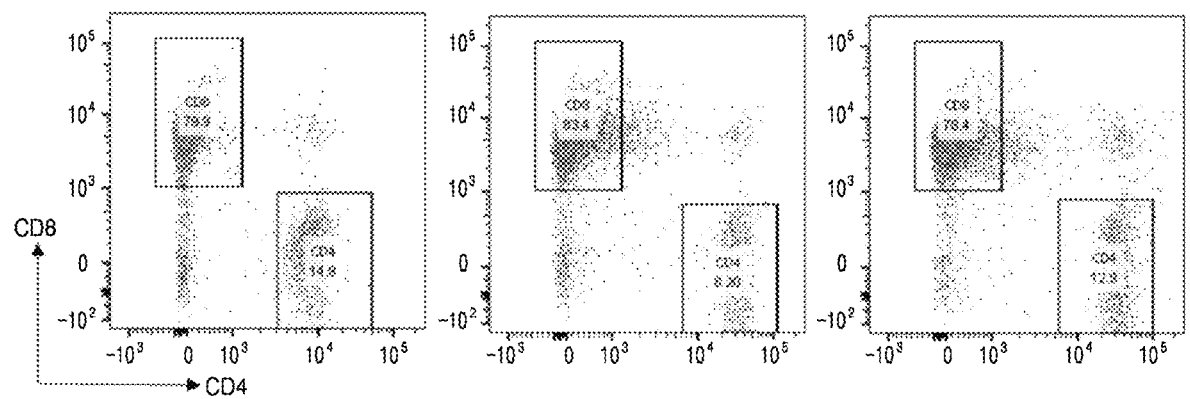
FIG. 9B is a diagram showing results of measuring ratios of CD4+ and CD8+ T cells among CD3 positive T cells.

Whether or not CAR was expressed was confirmed in the T cells into which the anti-MSLN-CAR prepared in Example 8-1 was introduced. Five days after the completion of lentiviral transduction of the T cells, some anti-MSLN-CAR-T cells were harvested, biotin-MSLN (Acrobiosystems or Biolegend) was added, and the cells were incubated on ice for 20 minutes, and then washed, and 1 μL of PE-anti-biotin was added and incubated on ice for 20 minutes. After washing the cells, CAR expression rates were confirmed by using FACS Canto II (BD), and the results are shown in FIG. 9A and Table 7. In addition, while culturing anti-MSLN-CAR-T for 14 days, expression of ultimately differentiated T cells (CD3) was analyzed by FACS, and the ratio of CD4+ and CD8+ T cells among CD3 positive T cells was measured, and the results are shown in FIG. 9B.

TABLE 7

| Clone | CAR expression % |
|---|---|
| CD19 (FMC63) | 50.8% |
| MSLN3 CAR scFv | 30.6% |

As confirmed in Table 7 and FIG. 9, as a result of confirming CAR expression rates of the prepared CAR-T, it was confirmed that the control group CD19 (FMC63)-CAR-T had a CAR expression rate of 50.8%, and MSLN3-CAR-T had an expression rate of 30.6%. As shown in FIG. 9, the ratio of CD4+:CD8+ as a result of the first round of transduction was measured to be 10%:80% on average.

Example 9: Confirmation of Cancer Cell Killing Effect of Anti-MSLN-CAR-T Cells Based on Tumor Animal Models 9-1: Administration of Anti-MSLN-CAR-T Cells to Tumor Animal Models An experiment was performed to confirm effectiveness of the MSLN3-CAR T cell therapeutic agent in ovarian cancer (OVCAR 3) animal models. Specifically, based on the cell killing effect of anti-MSLN3-CAR-T cells on cancer cells confirmed in Example 9, tumor ovarian cancer animal models were constructed to confirm the tumor killing ability.

In this test, 6-week-old female NOG (NOD/Shi-scid/IL-2Rγnull) specific-pathogen-free (SPF) mice were used, inspection and quarantine of the obtained animals were carried out by referring to the health monitoring report of the test system provided by the supplier, and the experiment was conducted after a week of acclimatization. The breeding environment for this test was at a temperature of 22±2° C., relative humidity of 50±10%, ventilation frequency 10 times to 20 times/hr, lighting time 12 hours (lights on at 8:00 am and off at 8:00 pm), and illumination of 150 lux to 300 lux, after high-pressure steam sterilization (121° C., sterilization time 20 minutes, drying time 5 minutes) of chip-type litter, an appropriate amount of the litter was placed in a polycarbonate breeding box (W 278 (mm)×L 420 (mm)×H 230 (mm)) and the mice were bred. For the feed supplied for the experiment, solid feed (+40 RMM-SP-10, U8239G10R, SAFE-DIETS, France) for laboratory animals sterilized by irradiation was used, and reverse osmosis (RO) water was put in a water bottle and sterilized with a high-pressure sterilizer, and the mice were allowed to drink freely.

The cells used in the ovarian cancer animal models were tested for *Mycoplasma pneumoniae*, Murine coronavirus (Mouse hepatitis virus, MHV), and Murine respirovirus (Sendai virus, SeV) and tested negative before use. The cells were cultured in a $CO_2$ incubator at 37° C. and 5% $CO_2$ by using a medium composed of RPMI 1640, 20% FBS, and 1% penicillin/streptomycin (P/S). RPMI 1640 (LM01 51, Welgene) medium was used. The composition of transplanted cancer cells and CAR-T cells and test groups are shown in Table 8 below.

For each cell, cell concentration was adjusted by using PBS, and 200 μL of each cells were subcutaneously implanted into mice, and the groups were separated by a random distribution method based on tumor sizes, for individual identification, the ear-punch method was used during the test period, and identification cards were attached to breeding boxes for each group.

9-2: Confirmation of Anticancer Effect of Anti-MSLN-CAR-T Cells Based on Tumor Animal Models After isolating the experimental groups, anti-MSLN-CAR-T cells were administered once through a tail vein, and the body weight, tumor size, tumor volume, and tumor weight of the test groups were measured twice a week starting from the day of initial administration.

Based on body weight on the day of initial administration, changes in body weight were observed until the day the test was ended. Body weight gain or loss (%) was calculated by using the equation below:

$$\text{Body weight change}(\%) = (\text{body weight/body weight at day 0}) \times 100 \quad \text{(Equation 1)}$$

Tumor volume ($mm^3$) was calculated by measuring a short axis (A) and a long axis (B) of tumor by using calipers and using the following equation:

$$\text{Tumor volume }(mm^3) = 1/2 \times [\{A(mm)\}^2 \times B(mm)] \quad \text{(Equation 2)}$$

For body weights and tumor volumes, after the last measurement, a statistical analysis was performed by using the post-hoc Dunnett's test of one-way ANOVA by comparing each HBSS-administered group with the anti-MSLN-CAR-T-administered group in ovarian cancer tumor models.

Figure 10:
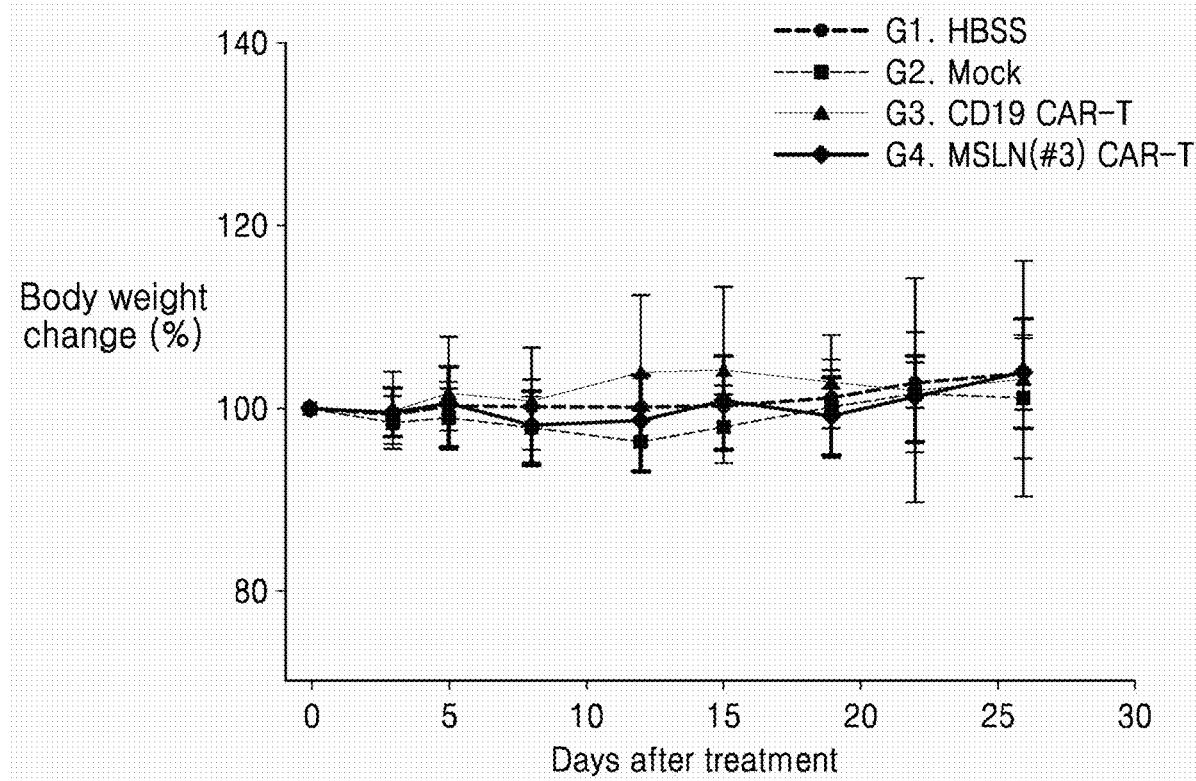
FIG. 10 is a diagram confirming changes by date in body weight of ovarian cancer (OVCAR-3) mouse models administered with HBSS (G1), Mock (G2), CD19-CAR-T (G3), and CAR-T cells (G4) into which anti-MSLN3-CAR was introduced.
Figure 11:
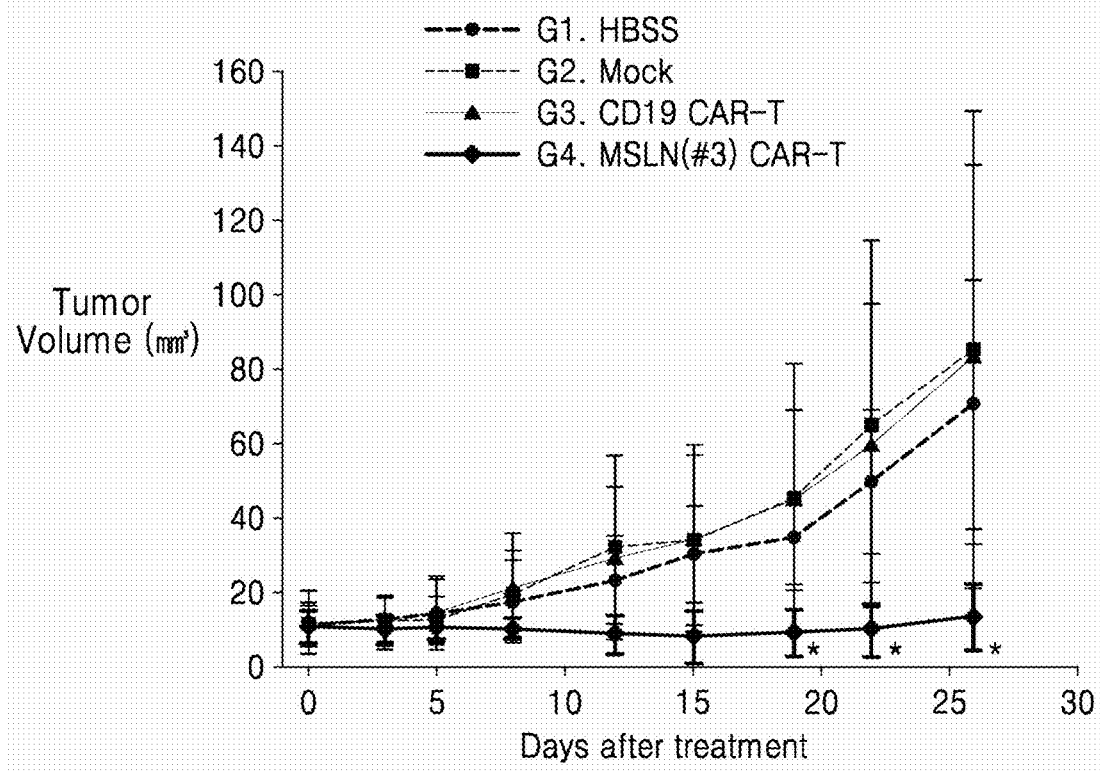
FIG. 11 is a diagram confirming changes in tumor volumes by date in ovarian cancer (OVCAR-3) mouse models administered with HBSS (G1), Mock (G2), CD19-CAR-T (G3), and CAR-T cells (G4) into which anti-MSLN3-CAR was introduced (*$p<0.05$ vs. the vehicle control treated group (G1))
Figure 12:
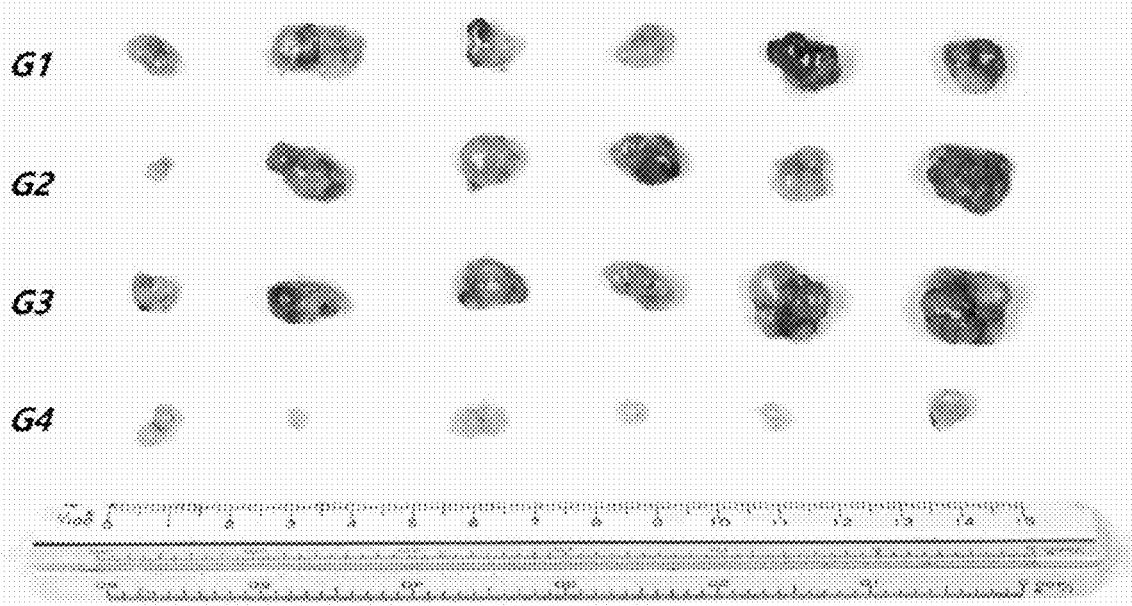
FIG. 12 is a diagram confirming tumor volumes on day 27 in ovarian cancer (OVCAR-3) mouse models administered with HBSS (G1), Mock (G2), CD19-CAR-T (G3), and CAR-T cells (G4) into which anti-MSLN3-CAR was introduced.
Figure 13:
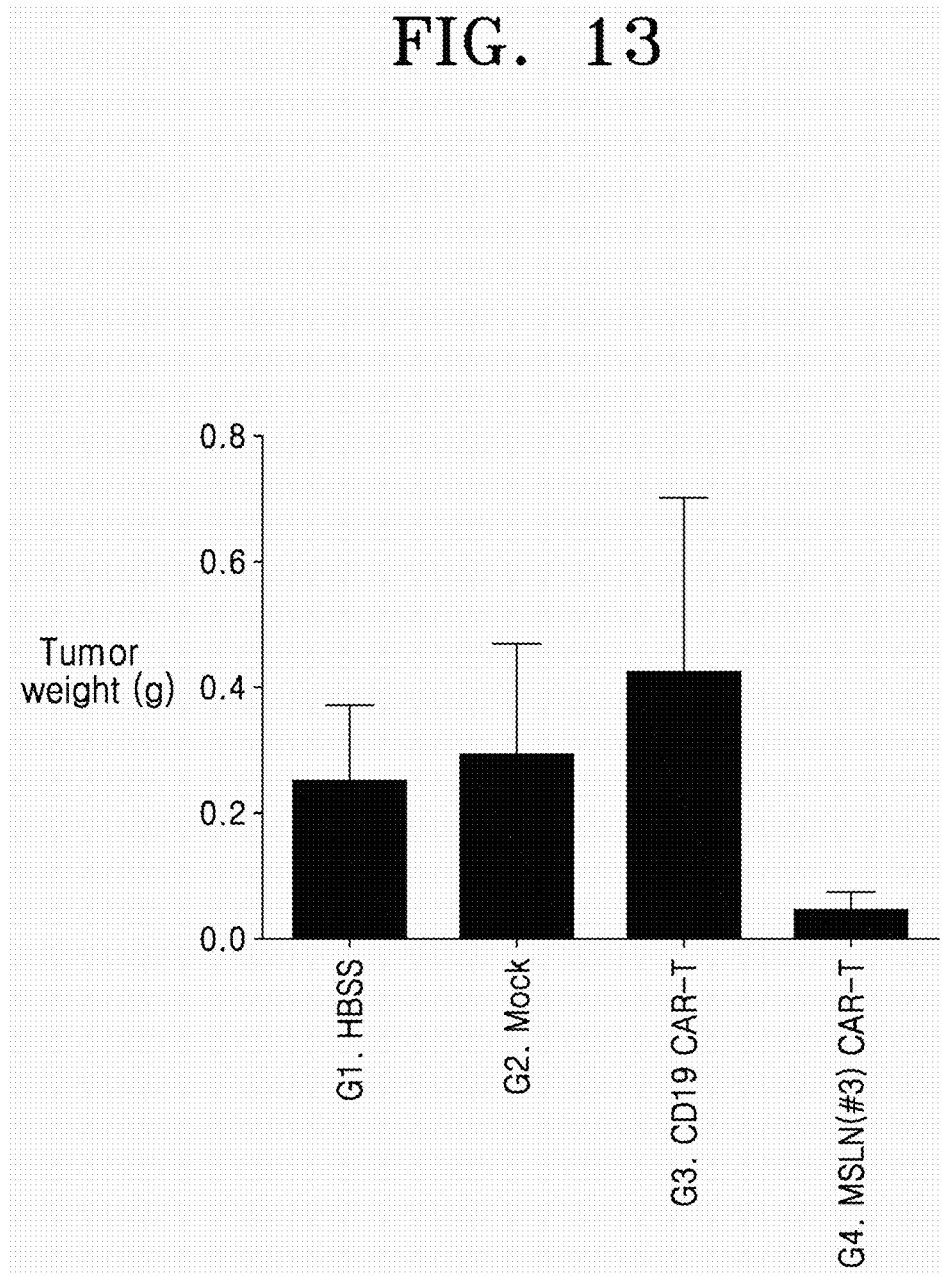
FIG. 13 is a diagram confirming tumor weights on day 27 in ovarian cancer (OVCAR-3) mouse models administered with HBSS (G1), Mock (G2), CD19-CAR-T (G3), and CAR-T cells (G4) into which anti-MSLN3-CAR was introduced.

Thereafter, results of confirming changes in body weight after the administration by dates are shown in FIG. 10, results of confirming changes in tumor volume after the administration by dates are shown in FIG. 11, results of confirming tumor volume on day 27 after a CAR-T administration for each group are shown in FIG. 12, and results of confirming tumor weight in the mouse models on day 27 after the CAR-T administration are shown in FIG. 13.

As confirmed in FIG. 10, no statistically significant weight change was observed in the group administered with anti-MSLN3-CAR-T cells compared to the control group G1 (HBSS-administered) administered with excipients, in the ovarian cancer tumor models. However, in a subject G3-4, weight loss was observed on day 26 after the administration, and body weight of the subject become less than 80% of the initial weight, and liver fibrosis was confirmed in the subject at autopsy.

As confirmed in FIG. 11, as a result of measuring tumor volumes, tumor volumes of the anti-MSLN3-CAR-T administered group, which is group G4, compared to that of groups G1, G2, and G3, hardly increased from the day of the administration, and the tumor was confirmed to be reduced from day 8 after the administration.

In addition, FIG. 12 shows results of visually confirming tumor sizes of each test group and a control group on day 27 after the administration of CAR-T cells, and as confirmed in FIG. 12, it was confirmed that the tumor size of group G4 was significantly smaller than that of the the control group G1.

TABLE 8

| Group | Number | Cell line (number of cells/animal) | Administered substance | Administration route | Dosage (CAR-T cells/animal) | Volume |
|---|---|---|---|---|---|---|
| G1 | 6 | OVCAR-3 (1 × 10⁷) | HBSS | I.V | — | 200 μL |
| G2 | 6 | | Mock | | — | |
| G3 | 6 | | CD19-CAR-T | | 5 × 10⁶ | |
| G4 | 6 | | antiMSLN3-CAR-T | | 5 × 10⁶ | |

As confirmed in FIG. 13, it was confirmed that tumor weight tended to significantly decrease in group G4 compared to group G1, which is the control group administered with excipients.

Overall, as a result of evaluating the tumor killing efficacy of anti-MSLN3-CAR-T cells in ovarian cancer models, compared to the HBSS-administered group, G1, it was confirmed that the tumor weight did not increase after an CAR-T administration, and the tumor volume, tumor size, and tumor weight also significantly decreased, and thus, a cancer cell killing effect of anti-MSLN3-CAR-T was confirmed in ovarian cancer animal models expressing mesothelin.

9-3: Confirmation of Infiltration into Tumor Through Immunohistochemical Staining of Anti-MSLN-CAR-T Cells Based on Tumor Animal Models After isolating the experimental groups, anti-MSLN-CAR-T cells were administered once tail vein, and 50 mg/kg of Zoletil™ and 10 mg/kg of Xylazine were intraperitoneally injected to induce anesthesia, the abdominal cavity was opened, blood was collected from the abdominal vena cava, and euthanasia was performed by exsanguination. Then, 3 per group were randomly selected, and then slides were prepared after fixing parts of the isolated tumor in 10% neutral formalin, and immunohistochemical (IHC) staining was performed for hCD3c (cell signaling, Cat. No 58061). Subsequently, the slides were photographed by using PANNORAMIC SCAN II (3DHISTECH, Hungary) and analyzed by using a 3DHISTECH software, and results of confirming the immunostaining of each group at 5× magnification and 20× magnification, are shown in FIGS. 14 and 15, respectively.

Figure 14:
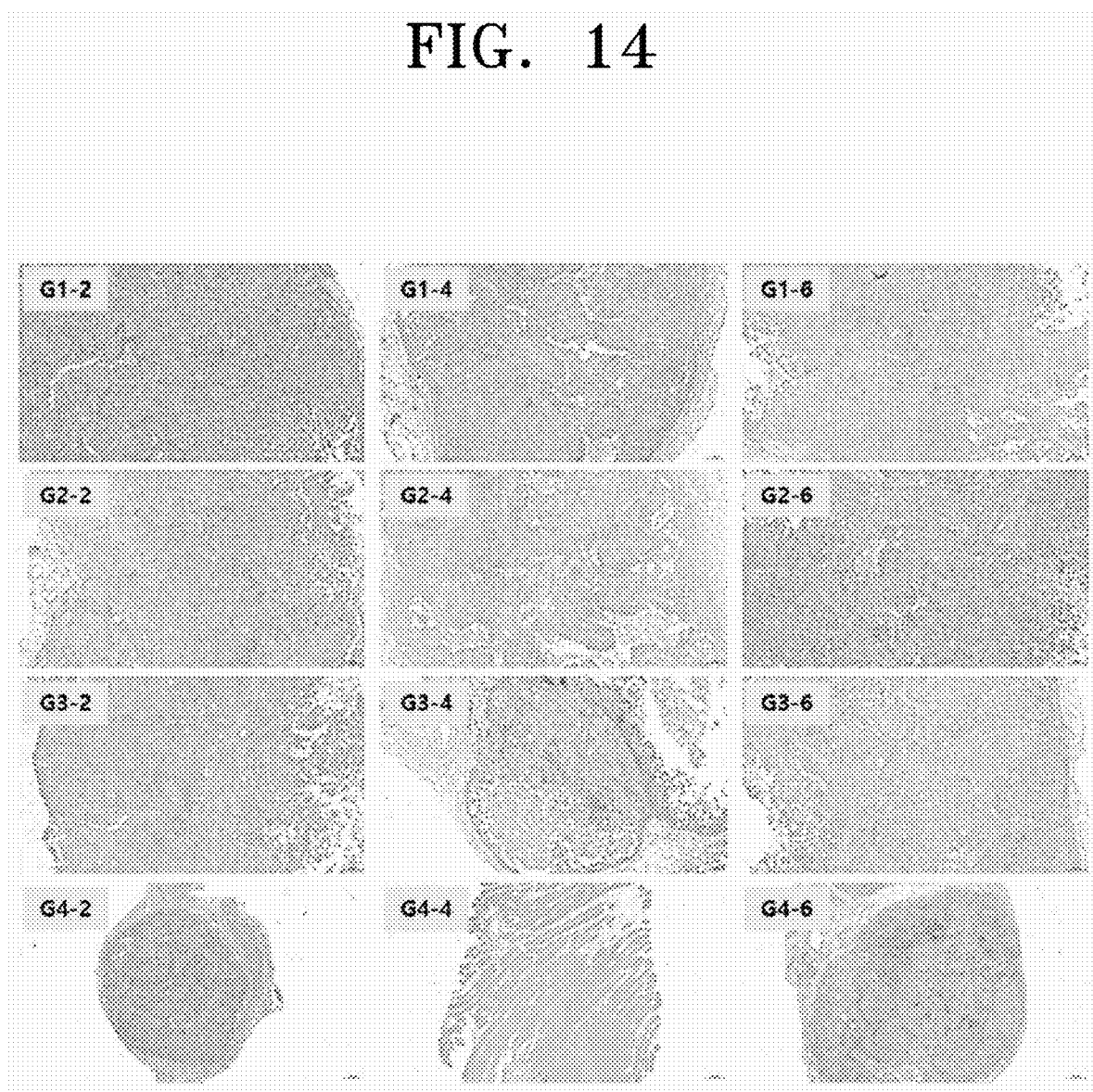
FIG. 14 is a diagram showing results of confirming results of immunohistochemical staining of ovarian cancer (OVCAR-3) mouse models administered with HBSS (G1), Mock (G2), CD19-CAR-T (G3), and CAR-T cells (G4) into which anti-MSLN3-CAR as introduced, at a magnification of 5×.
Figure 15:
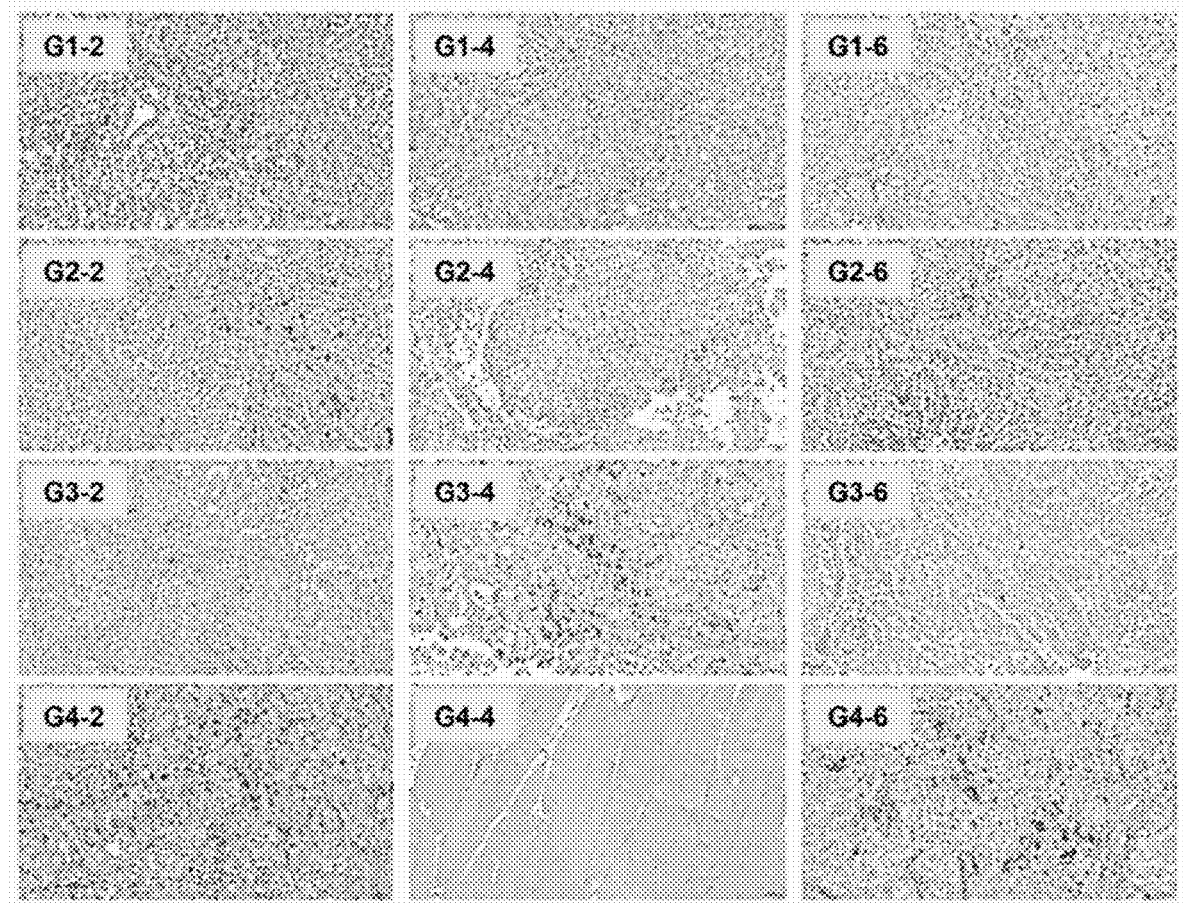
FIG. 15 is a diagram showing results of confirming results of immunohistochemical staining of ovarian cancer (OVCAR-3) mouse models administered with HBSS (G1), Mock (G2), CD19-CAR-T (G3), and CAR-T cells (G4) into which anti-MSLN3-CAR was introduced, at a magnification of 20×.

As confirmed in FIGS. 14 and 15, infiltration of T cells into tumor was confirmed in groups G2, G3, and G4, and thus, it was confirmed that the prepared MSLN-CAR-T cells effectively infiltrate T cells into tumor. In particular, a subject G4-4 was confirmed have tumor of a very small size at the time of autopsy, and complete response (CR) of the tumor was confirmed. In addition, in groups G1 and G3, necrosis was confirmed within the tumor. Therefore, overall, it was confirmed that T cell infiltration into tumors was observed to be relatively high in a large number of subjects in group G4, to which MSLN-CAR-T was administered.

The above description is for illustrative purposes, and those skilled in the art to which the present disclosure belongs will be able to understand that the examples and embodiments can be easily modified without changing the technical idea or essential features of the disclosure. Therefore, it should be understood that the above examples are not limitative, but illustrative in all aspects.

The invention claimed is:

1. An anti-mesothelin antibody or an antigen-binding fragment thereof, comprising:
   a heavy chain variable region comprising a heavy chain CDR1 comprising an amino acid sequence consisting of SEQ ID NO: 1; a heavy chain CDR2 comprising an amino acid sequence consisting of SEQ ID NO: 2; and a heavy chain CDR3 comprising an amino acid sequence consisting of SEQ ID NO: 3; and
   a light chain variable region comprising a light chain CDR1 comprising an amino acid sequence consisting of SEQ ID NO: 4; light chain CDR2 comprising an amino acid sequence consisting of SEQ ID NO: 5; and a light chain CDR3 comprising an amino acid sequence consisting of SEQ ID NO: 6.

2. The anti-mesothelin antibody or an antigen-binding fragment thereof according to claim 1, wherein the anti-mesothelin antibody or an antigen-binding fragment thereof comprises a heavy chain variable region comprising an amino acid sequence consisting of SEQ ID NO: 7.

3. The anti-mesothelin antibody or an antigen-binding fragment thereof according to claim 1, wherein the anti-mesothelin antibody or an antigen-binding fragment thereof comprises a light chain variable region comprising an amino acid sequence consisting of SEQ ID NO: 8.

4. The anti-mesothelin antibody or an antigen-binding fragment thereof according to claim 1, wherein the anti-mesothelin antibody or an antigen-binding fragment thereof comprises a heavy chain variable region comprising an amino acid sequence consisting of SEQ ID NO: 7 and a light chain variable region comprising an amino acid sequence consisting of SEQ ID NO: 8.

5. An isolated nucleic acid encoding an antibody or antigen-binding fragment thereof according to any one of claims 1-4.

6. A vector comprising an isolated nucleic acid according to claim 5.

7. An isolated host cell transformed with a vector according to claim 6.

8. A method for preparing an anti-mesothelin antibody or an antigen binding fragment thereof, comprising culturing a host cell according to claim 7 to express an antibody or an antigen binding fragment thereof.

9. A chimeric antigen receptor comprising an antigen-binding domain, a hinge domain, a transmembrane domain, and an intracellular signaling domain, wherein the antigen-binding domain is an anti-mesothelin antibody or an antigen-binding fragment thereof, comprising:
   a heavy chain variable region comprising a heavy chain CDR1 comprising an amino acid sequence consisting of SEQ ID NO: 1; a heavy chain CDR2 comprising an amino acid sequence consisting of SEQ ID NO: 2; and a heavy chain CDR3 comprising an amino acid sequence consisting of SEQ ID NO: 3; and
   a light chain variable region comprising a light chain CDR1 comprising an amino acid sequence consisting of SEQ ID NO: 4; a light chain CDR2 comprising an amino acid sequence consisting of SEQ ID NO: 5; and a light chain CDR3 comprising an amino acid sequence consisting of SEQ ID NO: 6.

10. The chimeric antigen receptor according to claim 9, wherein the antigen-binding domain comprises a heavy chain variable region comprising an amino acid sequence consisting of SEQ ID NO: 7 and a light chain variable region comprising an amino acid sequence consisting of SEQ ID NO: 8.

11. The chimeric antigen receptor according to claim 9, wherein the antigen-binding domain is a scFv (single chain variable fragment).

12. A nucleotide encoding a chimeric antigen receptor according to claim 9.

13. A vector comprising a nucleotide according to claim 12.

14. An isolated cell transformed with a vector according to claim 13.

15. The isolated cell according to claim 14, wherein the cell is a T cell, an NK cell, an NKT cell or a gamma delta (γδ) T cell.

16. A pharmaceutical composition for treating cancer, comprising an isolated cell according to claim 15.

* * * * *